US009102683B2

(12) United States Patent
Louie et al.

(10) Patent No.: US 9,102,683 B2
(45) Date of Patent: Aug. 11, 2015

(54) HETEROCYCLIC COMPOUNDS

(75) Inventors: Janis Louie, Salt Lake City, UT (US); Puneet Kumar, Salt Lake City, UT (US)

(73) Assignee: UNIVERSITY OF UTAH RESEARCH FOUNDATION, Salt Lake City, UT (US)

( * ) Notice: Subject to any disclaimer, the term of this patent is extended or adjusted under 35 U.S.C. 154(b) by 383 days.

(21) Appl. No.: 13/598,130

(22) Filed: Aug. 29, 2012

(65) Prior Publication Data
US 2013/0053553 A1    Feb. 28, 2013

Related U.S. Application Data

(60) Provisional application No. 61/528,739, filed on Aug. 29, 2011, provisional application No. 61/670,974, filed on Jul. 12, 2012.

(51) Int. Cl.
| | | |
|---|---|---|
| C07D 487/04 | (2006.01) | |
| C07D 487/10 | (2006.01) | |
| C07D 491/044 | (2006.01) | |
| C07D 491/04 | (2006.01) | |
| C07D 313/06 | (2006.01) | |
| C07D 225/04 | (2006.01) | |
| C07D 491/10 | (2006.01) | |

(52) U.S. Cl.
CPC ............ *C07D 491/04* (2013.01); *C07D 225/04* (2013.01); *C07D 313/06* (2013.01); *C07D 487/04* (2013.01); *C07D 487/10* (2013.01); *C07D 491/10* (2013.01)

(58) Field of Classification Search
None
See application file for complete search history.

(56) References Cited

U.S. PATENT DOCUMENTS 7,612,087 B2    11/2009    Aszodi et al.

OTHER PUBLICATIONS

Kumar. Angewandte Communications, 2012, 51, 8602-8606.*
Berge et al, 1977, "Pharmaceutically Acceptable Salts." J. Pharm. Sci. vol. 66, pp. 1-19.
Carruthers, "Some Modern Methods of Organic Synthesis, 3 Edition," Cambridge University Press, Cambridge, 1987.
Cesar, et al., "Trimethylsilyldiazomethane in the preparation of diazoketones via mixed anhydride and coupling reagent methods: a new approach to the Arndt—Eistert synthesis," Tet. Lett. 2001, 42, 7099-7102.
Creagh et al., "International Tables for Crystallography: mathematical, Physical and Chemical tables," vol. C, Chapter 4 Wilson, A. J. C., Ed.; Kluwer, Dordrecht, The Netherlands, 1992; pp. 206-222.
Duong et al., "Nickel-Catalyzed Cycloaddition of Alkynes and Isocyanates," J. Am. Chem. Soc. 2004, 126, 11438-11439.
Hashmi, et al., "Gold Catalysis: Domino Reaction of En-Diynes to Highly Substituted Phenols," Chem. Eur. J. 2011, 17, 8195-8201.
Hillier et al., "A One-Pot Preparation of 1,3-Disubstituted Azetidines," J. Org. Chem. 2006, 71, 7885-7887.
Kumar et al., "A Serendipitous Discovery: Nickel Catalyst for the Cycloaddition ofDiynes with Unactivated Nitriles," Angew. Chem. Int. Ed. 2011, 50, 10694-10698.
Kumar et al., "Ni-Catalyzed Ketene Cycloaddition: A System That Resists theFormation of Decarbonylation Side Products," J. Am. Chem. Soc. 2011, 133, 7719-7721.
Farrugia, "ORTEP-3 for Windows—a version of ORTEP-III with a Graphical User Interface (GUI)," J. Appl. Crystallogr. 1997, 30, 565.
Louie et al., "Efficient Nickel-Catalyzed [2+ 2+ 2] Cycloaddition of CO2 and Diynes," J. Am. Chem. Soc. 2002, 124, 15188-15189.
Loy et al., "Enantioselective Intramolecular Openings of Oxetanes Catalyzed by (salen)Co(III) Complexes: Access to Enantioenriched Tetrahydrofurans," J. Am. Chem. Soc. 2009, 131, 2786-2787.
Maslen et al. International Tables for Crystallography: Mathematical, Physical and Chemical Tables, vol. C, Chapter 6, Wilson, A. J. C., Ed.; Kluwer, Dordrecht, The Netherlands, 1992; pp. 476-516.
McDonald et al., "Rhodium-Catalyzed Alkyne Cyclotrimerization Strategies for C-Arylglycoside Synthesis," J. Am. Chem. Soc. 1995, 117, 6605-6606.
Otwinowski, Z.; Minor, W., "Processing of X-ray Diffraction Data Collected in Oscillation Mode", Methods Enzymol. 1997, 276, 307-326.
Podlech, et al., "Azetidin-3-ones from (S)-a:-Amino Acids and Their Reactions with Nucleophiles: Preparation of Some Azetidenite-Containing Amino-Alcohol and Amino-Acid Derivatives," Seebach, D. Helv. Chim. Acta 1995, 78, 1238-1246.
Altomare et al., "SIR92—A program for automatic solution and refinement of crystal structure." J. Appl. Cryst. (1994). 27, 435.
Sperger, et al., "Gold-Catalyzed Tandem Cyclizations of 1,6-Diynes Triggered by Internal N- and O-Nucleophiles," J. Org. Chem. 2010, 75, 4542-4553.
Zhang et al., "Rhodium-Catalyzed Decarboxylative Cycloaddition Route toSubstituted Anilines," J. Org. Chem. 2011, 76, 4686-4691.
Sorrell, "Organic Chemistry," Journal of Chemical Education, vol. 77, No. 1, Jan. 2000, p. 31.
Poste et al., "Lipid Vesicles as Carriers for Introducing Biologically Active Materials into Cells," Prescott, Ed., Methods in Cell Biology, vol. XIV, Academic Press, New York, N.Y., (1976) p. 33-71.
United States Patent Office Action for U.S. Appl. No. 13/598,116 dated Jun. 24, 2014 (8 pages).
Chang, L. W., "The neurotoxicology and pathology of organomercury, organolead and organotin" Journal of Toxicological Sciences, 1990, 15 (Suppl. 4) 125-51.
United States Patent Office Final Rejection for U.S. Appl. No. 13/598,116 dated Nov. 6, 2014 (9 pages).
Katvalyan, G. T. "Regiospecific cyclization of 3-aza-1, 5-diketones to 4, 5 dehydro-3-piperidinones," Izvestiya Akademii Nauk SSSR, Seriya Khimicheskaya 1976, (2), 468-71 (abstract only).
Greene and Wuts, Protective Groups in Organic Synthesis 3rd edition Wiley: New York, 1999, pp. 494-615.
RN 1177770-96-5, 4-(aminomethyl)-1, 6-dihydro-1, 2-dimethyl-5-[(phosphonooxy)methyl]- (2H)- Pyridin-3-one, Entered STN: Aug. 30, 2009.

(Continued)

*Primary Examiner* — Noble Jarrell
(74) *Attorney, Agent, or Firm* — Michael Best & Friedrich LLP

(57) ABSTRACT

Described herein are methods for synthesizing heterocyclic, 8-membered ring structures. The methods may allow for preparation of highly substituted 8-membered rings. Also disclosed are heterocyclic, 8-membered ring compounds and pharmaceutical compositions comprising the compounds.

18 Claims, 1 Drawing Sheet

(56) References Cited

OTHER PUBLICATIONS

Yip "Aerobic Oxidative cyclization under Pd (II) catalysis. A regioselective approach to heterocycles," Organic Letters, 2005, 7(25), 5717-5719.

United States Patent Office Action for U.S. Appl. No. 13/598,116 dated Apr. 2, 2015 (11 pages).
Donohoe, "Synthesis of substituted pyridines and pyridazines via ring closing metathesis," Chemical Communications, 2009, 21, 3008-3010.

* cited by examiner

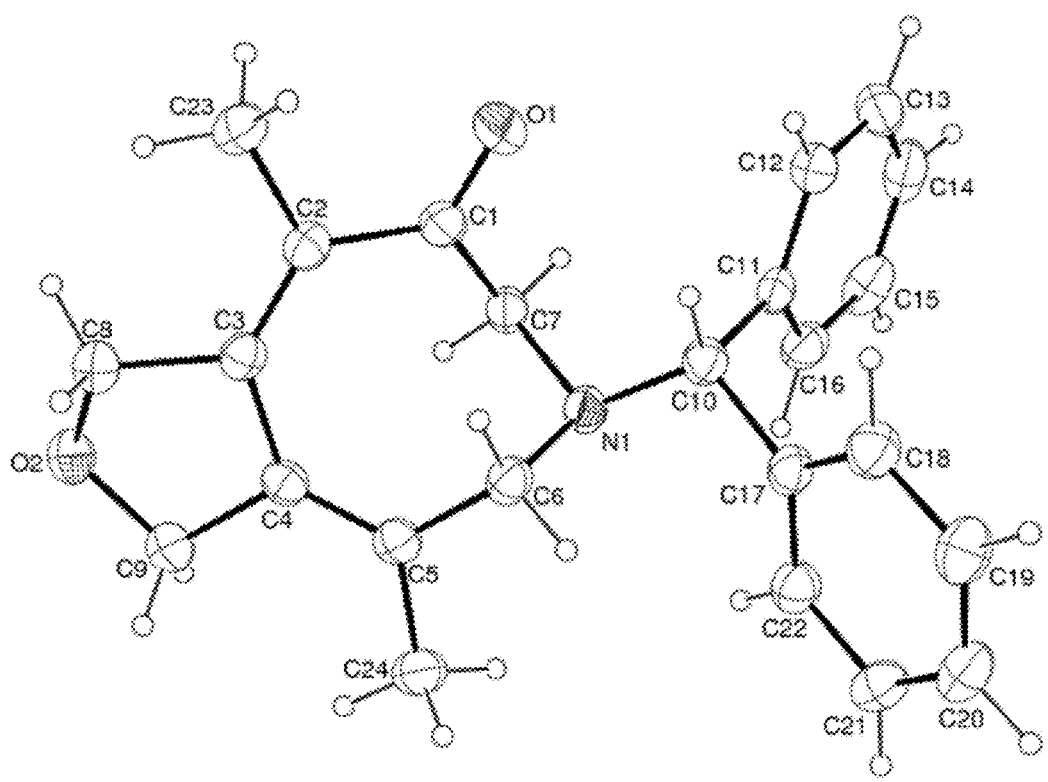

HETEROCYCLIC COMPOUNDS

CROSS-REFERENCE TO RELATED APPLICATIONS

This application claims priority to U.S. Provisional Patent Application No. 61/528,739, filed on Aug. 29, 2011, and U.S. Provisional Patent Application No. 61/670,974, filed on Jul. 12, 2012, the entire contents of each which are hereby incorporated by reference.

STATEMENT REGARDING FEDERALLY SPONSORED RESEARCH

This invention was made with U.S. Government support awarded by the National Science Foundation, Grant No. 0911017. The U.S. Government has certain rights in this invention.

BACKGROUND

Although significant progress has been made in the area of C—H bond activation, C—C bond activation is still relatively dormant. This may be attributed to the highly inert nature of the C—C sigma bond in addition to a poor interaction of the orbitals of the C—C sigma bond and transition metals.

While medium-sized heterocycles are prevalent in numerous bioactive molecules, the synthesis of eight-membered rings poses a serious challenge due to disfavored enthalpic and entropic factors. There is a continuing need for new synthetic methodologies that will enable efficient C—C bond activation, and for methodologies that allow for effective synthesis of eight-membered ring systems.

SUMMARY

In one aspect, this disclosure provides a method of synthesizing a compound of formula (I):

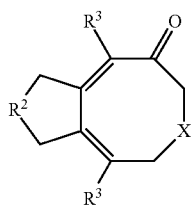

(I)

wherein:

X is selected from the group consisting of O and NR$^1$;

R$^1$ is selected from the group consisting of hydrogen, alkyl, and a nitrogen protecting group;

R$^2$ is selected from the group consisting of —C(O)O—, —C(O)—, —O—, —NR$^4$— and —CR$^5_2$—;

each R$^3$ is independently selected from the group consisting of hydrogen, alkyl, alkenyl, alkynyl, cycloalkyl, heterocyclyl, aryl, heteroaryl and cyano, any of which may be optionally substituted;

R$^4$ is selected from the group consisting of hydrogen, alkyl, and a nitrogen protecting group; and each R$^5$ is independently selected from the group consisting of hydrogen, alkyl, alkenyl, alkynyl, cycloalkyl, heterocyclyl, aryl, heteroaryl, acyl, alkoxy, amido, amino, carboxy, cyano, ester, halo, haloalkyl, hydroxy, nitro, phosphonate, sulfinyl, sulfonyl, sulfonate, sulfonamino and sulfonamido, any of which may be optionally substituted; or two R$^5$ are taken together with the atom to which they are attached to form an optionally substituted ring system;

the method comprising combining the following components to form a reaction mixture:

a) a compound of formula (II):

(II)

b) a compound of formula (III):

(III)

c) a nickel-containing compound; and d) a ligand.

In another aspect, this disclosure provides a compound of formula (I):

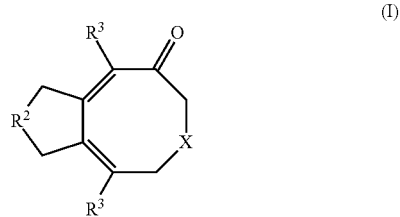

(I)

wherein:

X is selected from the group consisting of O and NR$^1$;

R$^1$ is selected from the group consisting of hydrogen, alkyl, and a nitrogen protecting group;

R$^2$ is selected from the group consisting of —C(O)O—, —C(O)—, —O—, —NR$^4$— and —CR$^5_2$—;

each R$^3$ is independently selected from the group consisting of hydrogen, alkyl, alkenyl, alkynyl, cycloalkyl, heterocyclyl, aryl, heteroaryl and cyano, any of which may be optionally substituted;

R$^4$ is selected from the group consisting of hydrogen, alkyl, and a nitrogen protecting group; and each R$^5$ is independently selected from the group consisting of hydrogen, alkyl, alkenyl, alkynyl, cycloalkyl, heterocyclyl, aryl, heteroaryl, acyl, alkoxy, amido, amino, carboxy, cyano, ester, halo, haloalkyl, hydroxy, nitro, phosphonate, sulfinyl, sulfonyl, sulfonate, sulfonamino and sulfonamido, any of which may be optionally substituted; or two R$^5$ are taken together with the atom to which they are attached to form an optionally substituted ring system.

Other aspects and embodiments will become apparent in light of the following description and drawings.

BRIEF DESCRIPTION OF THE DRAWINGS

FIG. 1 shows an Oak Ridge Thermal Ellipsoid Plot (ORTEP) of compound 3dd, described herein, which was characterized by single-crystal X-ray crystallography.

DETAILED DESCRIPTION

Described herein are methods of synthesizing eight-membered heterocyclic ring systems, including highly substituted eight-membered heterocycles. The heterocycles may be effectively produced in one step, by coupling a diyne with a 3-azetidinone or 3-oxetanone compound in the presence of a nickel-containing compound and a ligand. The methodology may be of great use in developing new pharmaceutical compounds.

1. DEFINITIONS

The terminology used herein is for the purpose of describing particular embodiments only and is not intended to be limiting. As used in the specification and the appended claims, the singular forms "a," "and" and "the" include plural references unless the context clearly dictates otherwise.

Section headings as used in this section and the entire disclosure herein are not intended to be limiting.

For the recitation of numeric ranges herein, each intervening number there between with the same degree of precision is explicitly contemplated. For example, for the range 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6.9 and 7.0 are explicitly contemplated.

As used herein, the term "about" is used synonymously with the term "approximately." Illustratively, the term "about," as used in connection with a particular value, indicates that the value may be slightly outside the particular value. Variation may be due to conditions such as experimental error, manufacturing tolerances, variations in equilibrium conditions, and the like. In some embodiments, the term "about" includes the cited value plus or minus 10%. Such values are thus encompassed by the scope of the claims reciting the terms "about" and "approximately."

Definitions of specific functional groups and chemical terms are described in more detail below. For purposes of this disclosure, the chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; Carruthers, *Some Modern Methods of Organic Synthesis*, 3$^{rd}$ Edition, Cambridge University Press, Cambridge, 1987; the entire contents of each of which are incorporated herein by reference.

The term "acyl" refers to an alkylcarbonyl, cycloalkylcarbonyl, heterocyclylcarbonyl, arylcarbonyl or heteroarylcarbonyl substituent, any of which may be further substituted (e.g., with one or more substituents).

The term "alkyl" refers to a straight or branched saturated hydrocarbon chain. Alkyl groups may include a specified number of carbon atoms. For example, $C_1$-$C_{12}$ alkyl indicates that the alkyl group may have 1, 2, 3, 4, 5, 6, 7, 8, 9, 10, 11 or 12 carbon atoms. An alkyl group may be, e.g., a $C_1$-$C_{12}$ alkyl group, a $C_1$-$C_{10}$ alkyl group, a $C_1$-$C_8$ alkyl group, a $C_1$-$C_6$ alkyl group or a $C_1$-$C_4$ alkyl group. For example, exemplary $C_1$-$C_4$ alkyl groups include methyl, ethyl, n-propyl, isopropyl, n-butyl, sec-butyl, isobutyl and tert-butyl groups. An alkyl group may be optionally substituted with one or more substituents.

The term "alkenyl" refers to a straight or branched hydrocarbon chain having one or more double bonds. Alkenyl groups may include a specified number of carbon atoms. For example, $C_2$-$C_{12}$ alkenyl indicates that the alkenyl group may have 2, 3, 4, 5, 6, 7, 8, 9, 10, 11 or 12 carbon atoms. An alkenyl group may be, e.g., a $C_2$-$C_{12}$ alkenyl group, a $C_2$-$C_{10}$ alkenyl group, a $C_2$-$C_8$ alkenyl group, a $C_2$-$C_6$ alkenyl group or a $C_2$-$C_4$ alkenyl group. Examples of alkenyl groups include but are not limited to allyl, propenyl, 2-butenyl, 3-hexenyl and 3-octenyl groups. One of the double bond carbons may optionally be the point of attachment of the alkenyl substituent. An alkenyl group may be optionally substituted with one or more substituents.

The term "alkynyl" refers to a straight or branched hydrocarbon chain having one or more triple bonds. Alkynyl groups may include a specified number of carbon atoms. For example, $C_2$-$C_{12}$ alkynyl indicates that the alkynyl group may have 2, 3, 4, 5, 6, 7, 8, 9, 10, 11 or 12 carbon atoms. An alkynyl group may be, e.g., a $C_2$-$C_{12}$ alkynyl group, a $C_2$-$C_{10}$ alkynyl group, a $C_2$-$C_8$ alkynyl group, a $C_2$-$C_6$ alkynyl group or a $C_2$-$C_4$ alkynyl group. Examples of alkynyl groups include but are not limited to ethynyl, propargyl, and 3-hexynyl. One of the triple bond carbons may optionally be the point of attachment of the alkynyl substituent. An alkynyl group may be optionally substituted with one or more substituents.

The term "aryl" refers to an aromatic monocyclic, bicyclic, or tricyclic hydrocarbon ring system, wherein any ring atom capable of substitution may be substituted (e.g., with one or more substituents). Examples of aryl moieties include but are not limited to phenyl, naphthyl, and anthracenyl. Aryl groups may be optionally substituted with one or more substituents.

The term "arylalkyl" refers to an alkyl moiety in which at least one alkyl hydrogen atom is replaced with an aryl group. Arylalkyl includes groups in which more than one hydrogen atom has been replaced with an aryl group. Examples of arylalkyl groups include but are not limited to benzyl, 2-phenylethyl, 3-phenylpropyl, 9-fluorenyl, benzhydryl, and trityl groups. Arylalkyl groups may be optionally substituted with one or more substituents, on either the aryl moiety or the alkyl moiety.

The term "cycloalkyl" as used herein refers to non-aromatic, saturated or partially unsaturated cyclic, bicyclic, tricyclic or polycyclic hydrocarbon groups having 3 to 12 carbons. Any ring atom may be substituted (e.g., with one or more substituents). Cycloalkyl groups may contain fused rings. Fused rings are rings that share one or more common carbon atoms. Examples of cycloalkyl groups include but are not limited to cyclopropyl, cyclobutyl, cyclopentyl, cyclohexyl, cyclohexenyl, cyclohexadienyl, methylcyclohexyl, adamantyl, norbornyl, norbornenyl, tetrahydronaphthalenyl and dihydroindenyl. Cycloalkyl groups may be optionally substituted with one or more substituents.

The term "halo" or "halogen" as used herein refers to any radical of fluorine, chlorine, bromine or iodine.

The term "haloalkyl" as used herein refers to an alkyl group as defined herein, such as a $C_1$-$C_4$ alkyl group, in which one or more hydrogen atoms are replaced with halogen atoms, and includes alkyl moieties in which all hydrogens have been replaced with halogens (e.g., perfluoroalkyl such as $CF_3$).

The term "heteroaryl" as used herein refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms independently selected from O, N, S, P and Si (e.g., carbon atoms and 1-3, 1-6, or 1-9 heteroatoms independently selected from O, N, S, P and Si if monocyclic, bicyclic, or tricyclic, respectively). Any ring atom may be substituted (e.g., with one or more substituents). Heteroaryl groups may contain fused rings, which are rings that share one or more common atoms. Examples of heteroaryl groups include but are not limited to radicals of pyridine, pyrimidine, pyrazine, pyridazine, pyrrole, imidazole, pyrazole, oxazole, isoxazole, furan, thiazole, isothiazole, thiophene, quinoline, isoquinoline, quinoxaline, quinazoline, cinnoline, indole, isoindole, indolizine, indazole, benzimidazole, phthalazine, pteridine, carbazole, carboline, phenanthridine, acridine, phenanthroline, phenazine, naphthyridines and purines. Heteroaryl groups may be optionally substituted with one or more substituents.

The term "heteroatom", as used herein, refers to a non-carbon or hydrogen atom such as a nitrogen, sulfur, oxygen, silicon or phosphorus atom. Groups containing more than one heteroatom may contain different heteroatoms.

The term "heterocyclyl", as used herein, refers to a non-aromatic, saturated or partially unsaturated 3-10 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, S, Si and P (e.g., carbon atoms and 1-3, 1-6, or 1-9 heteroatoms of O, N, S, Si and P if monocyclic, bicyclic, or tricyclic, respectively). Any ring atom may be substituted (e.g., with one or more substituents). Heterocyclyl groups may contain fused rings, which are rings that share one or more common atoms. Examples of heterocyclyl groups include but are not limited to radicals of tetrahydrofuran, tetrahydrothiophene, tetrahydropyran, oxetane, piperidine, piperazine, morpholine, pyrroline, pyrimidine, pyrrolidine, indoline, tetrahydropyridine, dihydropyran, thianthrene, pyran, benzopyran, xanthene, phenoxathiin, phenothiazine, furazan, lactones, lactams such as azetidinones and pyrrolidinones, sultams, sultones, and the like. Heterocyclyl groups may be optionally substituted with one or more substituents.

The term "hydroxy" refers to an —OH radical. The term "alkoxy" refers to an —O-alkyl radical. The term "aryloxy" refers to an —O-aryl radical. The alkyl portion of an alkoxy group or the aryl portion of an aryloxy group may be optionally substituted with one or more substituents. (For example, "alkoxy" encompasses hydroxyalkoxy groups, in which the alkyl portion of the alkoxy group is substituted with a hydroxy group.)

The term "ligand" refers to an organic molecule comprising at least one unshared electron pair that is available for donation to a metal atom. The unshared electron pair may reside on, for example, a nitrogen, phosphorus, arsenic, oxygen, sulfur or carbon atom.

The term "nitrogen protecting group" refers to a moiety that is used to temporarily block a desired nitrogen functional groups in a compound, e.g., a compound with multiple reactive sites. The nitrogen protecting group may protect a nitrogen atom from undesirable chemical reactions under specified conditions (e.g., pH, temperature, radiation, solvent, and the like). In some embodiments, a protecting group has one, or more, or all of the following characteristics: a) it may be added selectively to a nitrogen functional group in good yield to give a protected compound; b) it is stable to reactions occurring at one or more reactive sites in the molecule; and c) it is selectively removable in good yield by reagents that do not attack the regenerated, deprotected nitrogen functional group. Nitrogen protecting groups include but are not limited to: acetyl (Ac), allyloxycarbonyl (Alloc), benzyl (Bn), benzhydryl (Bnh), benzoyl (Bz), tert-butyloxycarbonyl (Boc), 2-biphenyl-2-propoxycarbonyl (Bpoc), carbobenzyloxy (Cbz), 3,4-dimethoxybenzyl (DMPM), 9-fluorenylmethyloxycarbonyl (FMOC), p-methoxybenzylcarbonyl (Moz), 2- or 4-nitrobenzenesulfonyl (nosyl, Ns), o-nitrophenylsulfenyl (Nps), 2-(phenylsulfonyl)ethyloxycarbonyl (Psec), p-ethoxybenzyl (PMB), p-methoxyphenyl (PMP), p-toluenesulfonyl (tosyl, Ts), 6-nitroveratryloxycarbonyl (Nvoc), 2-trimethylsilylethyloxycarbonyl (Teoc) and 2,2,2-trichloroethyloxycarbonyl (Troc), and, in suitable cases (e.g., cyclic amines), a nitroxide radical. Other examples may be found in, for example, *Protective Groups in Organic Synthesis* (T. Green and P. Wuts; 3rd Edition; John Wiley and Sons, 1999).

The term "oxo" refers to an oxygen atom, which forms a carbonyl when attached to carbon, an N-oxide when attached to nitrogen, and a sulfoxide or sulfone when attached to sulfur (i.e. =O).

The term "mercapto" or "thiol" refers to an —SH radical. The term "thioalkoxy" or "thioether" refers to an —S-alkyl radical. The term "thioaryloxy" refers to an —S-aryl radical.

The term "substituents" refers to a group "substituted" on an alkyl, alkenyl, alkynyl, cycloalkyl, heterocyclyl, aryl, arylalkyl, heteroaryl or heteroarylalkyl group at any atom of that group. Any atom may be substituted. Suitable substituents include, without limitation: acyl, acylamido, acyloxy, alkoxy, alkyl, alkenyl, alkynyl, amido, amino, carboxy, cyano, ester, halo, haloalkyl, hydroxy, imino, nitro, oxo (e.g., C=O), phosphonate, sulfinyl, sulfonyl, sulfonate, sulfonamino, sulfonamido, thioamido, thiol, thioxo (e.g., C=S), and ureido. In embodiments, substituents on a group are independently any one single, or any combination of the aforementioned substituents. In embodiments, a substituent may itself be substituted with any one of the above substituents.

The above substituents may be abbreviated herein. For example, the abbreviations Me, Et, Ph and Bn represent methyl, ethyl, phenyl and benzyl, respectively. A more comprehensive list of standard abbreviations used by organic chemists appears in a table entitled Standard List of Abbreviations of the Journal of Organic Chemistry. The abbreviations contained in said list are hereby incorporated by reference.

For compounds described herein, groups and substituents thereof may be selected in accordance with permitted valence of the atoms and the substituents, and such that the selections and substitutions result in a stable compound, e.g., a compound that does not spontaneously undergo transformation such as by rearrangement, cyclization, elimination, etc.

Where substituent groups are specified by their conventional chemical formulae, written from left to right, they optionally encompass substituents resulting from writing the structure from right to left, e.g., —CH$_2$O— optionally also recites —OCH$_2$—.

In accordance with a convention used in the art, the group:

is used in structural formulae herein to depict the bond that is the point of attachment of the moiety or substituent to the core or backbone structure.

2. METHODS OF SYNTHESIZING COMPOUNDS

This disclosure provides methods of synthesizing compounds of formula (I), which may proceed via coupling of a 3-azetidinone or a 3-oxetanone with a diyne. In particular, the disclosure provides a method of synthesizing a compound of formula (I):

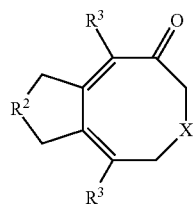

(I)

wherein:
X is selected from the group consisting of O and NR$^1$;
R$^1$ is selected from the group consisting of hydrogen, alkyl, and a nitrogen protecting group;
R$^2$ is selected from the group consisting of —C(O)O—, —C(O)—, —O—, —NR$^4$— and —CR$^5_2$—;
each R$^3$ is independently selected from the group consisting of hydrogen, alkyl, alkenyl, alkynyl, cycloalkyl, heterocyclyl, aryl, heteroaryl and cyano, any of which may be optionally substituted;
R$^4$ is selected from the group consisting of hydrogen, alkyl, and a nitrogen protecting group; and
each R$^5$ is independently selected from the group consisting of hydrogen, alkyl, alkenyl, alkynyl, cycloalkyl, heterocyclyl, aryl, heteroaryl, acyl, alkoxy, amido, amino, carboxy, cyano, ester, halo, haloalkyl, hydroxy, nitro, phosphonate, sulfinyl, sulfonyl, sulfonate, sulfonamino and sulfonamido, any of which may be optionally substituted; or two R$^5$ are taken together with the atom to which they are attached to form an optionally substituted ring system;
the method comprising combining the following components to form a reaction mixture:
a) a compound of formula (II):

(II)

b) a compound of formula (III):

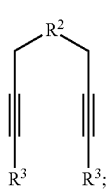

(III)

c) a nickel-containing compound; and
d) a ligand.

a. Compounds of Formula (II)

One of the starting materials in the methods of synthesis described herein is a compound of formula (II):

(II)

wherein:
X is selected from the group consisting of O and NR$^1$;
R$^1$ is selected from the group consisting of hydrogen, alkyl, and a nitrogen protecting group.

In some embodiments, X is O. In some embodiments, X is NR$^1$. In some embodiments, R$^1$ is alkyl. In some embodiments, R$^1$ is a nitrogen protecting group, such as, e.g., tert-butyloxycarbonyl (Boc) or benzhydryl (Bnh).

Suitable compounds of formula (II) include, but are not limited to, 1-Boc-3-azetidinone, 1-benzhydryl-3-azetidinone, and 3-oxetanone. Such compounds may be commercially available from a variety of sources (e.g., Sigma-Aldrich, St. Louis, Mo.), or may be synthesized by any means known in the art. For example, 3-azetidinone may be N-protected using any suitable protecting group reagent.

In some embodiments, compounds of formula (II) may be further substituted, e.g., with a substituent in the 2-position of the azocine or oxetanone. In some embodiments, use of such compounds may lead to formation of enantiopure products.

b. Compounds of Formula (III)

Another starting material in the methods of synthesis described herein is a compound of formula (III):

(III)

wherein:
R$^2$ is selected from the group consisting of —C(O)O—, —C(O)—, —O—, —NR$^4$— and —CR$^5_2$—;
each R$^3$ is independently selected from the group consisting of hydrogen, alkyl, alkenyl, alkynyl, cycloalkyl, heterocyclyl, aryl, heteroaryl and cyano, any of which may be optionally substituted;
R$^4$ is selected from the group consisting of hydrogen, alkyl, and a nitrogen protecting group; and
each R$^5$ is independently selected from the group consisting of hydrogen, alkyl, alkenyl, alkynyl, cycloalkyl, heterocyclyl, aryl, heteroaryl, acyl, alkoxy, amido, amino, carboxy, cyano, ester, halo, haloalkyl, hydroxy, nitro, phosphonate, sulfinyl, sulfonyl, sulfonate, sulfonamino and sulfonamido, any of which may be optionally substituted; or two R$^5$ are taken together with the atom to which they are attached to form an optionally substituted ring system.

In some embodiments, R$^2$ is selected from the group consisting of —O—, —NR$^4$— and —CR$^5_2$—. In some embodiments, R$^2$ is O.

In some embodiments, $R^2$ is $-NR^4-$. In some embodiments, $R^4$ is a nitrogen protecting group, such as, e.g., tert-butyloxycarbonyl (Boc) or tosyl (Ts).

In some embodiments, $R^2$ is $-CR^5_2-$. In some embodiments, the two $R^5$ groups are the same. In some embodiments, the two $R^5$ groups are different.

In some embodiments, each $R^5$ is independently selected from the group consisting of hydrogen, $C_1$-$C_6$ alkyl (e.g., $C_1$-$C_4$ alkyl such as methyl, ethyl, isopropyl, n-propyl and tert-butyl), including substituted $C_1$-$C_6$ alkyl groups (e.g., an alkoxyalkyl group such as methoxymethyl), ester (e.g., a methyl ester or $-C(O)OCH_3$), sulfonyl (e.g., $-SO_2Ph$), aryl (e.g., phenyl), and cyano.

In some embodiments, both $R^5$ are taken together with the atom to which they are attached to form an optionally substituted ring. In some embodiments, both $R^5$ are taken together with the atom to which they are attached to form a monocyclic 4-, 5- or 6-membered ring. In some embodiments, two $R^5$ are taken together with the atom to which they are attached to form a ring that is fused to an additional ring, e.g., to make a bicyclic ring system. In some embodiments, both $R^5$ are taken together with the atom to which they are attached to form a ring selected from the group consisting of: a dioxane ring, which may be substituted (e.g., 2,2-dimethyl-1,3-dioxane-4,6-dione); an indane ring, which may be substituted (e.g., 1H-indene-1,3(2H)-dione); an oxetane ring; and an azetidine ring, such as a protected azetidine ring (e.g., 1-benzhydry-lazetidine).

Suitable compounds of formula (III) include, but are not limited to, the following:

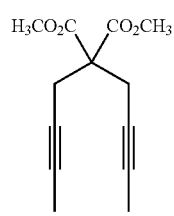

1a

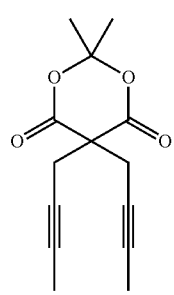

1b

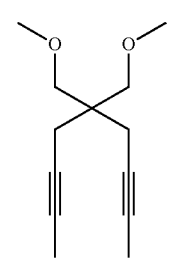

1c

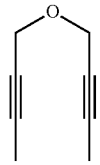

1d

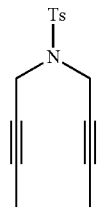

1e

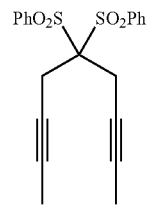

1f

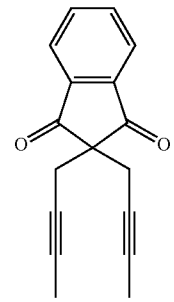

1g

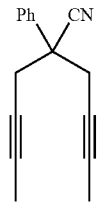

1h

1i

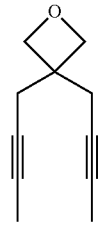

1j

-continued

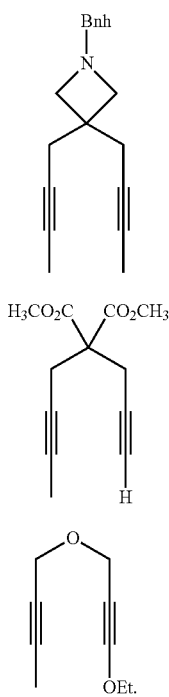

1k

1l

1m

Such compounds may be commercially available from a variety of sources (e.g., Sigma-Aldrich, St. Louis, Mo.), or may be synthesized by any means known in the art.

A compound of formula (III) may be included in a reaction at an amount of about 1.0 to about 5.0 equivalents compared to the compound of formula (II). For example, about 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9 or 5.0 equivalents of the compound of formula (III) may be used compared to the compound of formula (II). By way of another example, if 1.0 mmol of a compound of formula (II) is included in a reaction mixture, then about 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9 or 5.0 mmol of the compound of formula (III) may be included in the reaction mixture.

c. Nickel-Containing Compounds

Another starting material in the methods of synthesis described herein is a nickel-containing compound. For example, the nickel-containing compound may include Ni(0). A suitable source of Ni(0) is bis(cyclooctadiene)nickel (0).

A nickel-containing compound may be included in a reaction mixture in an amount of about 1 mol % to about 20 mol %, e.g., about 5 mol % to about 15 mol %. For example, a nickel-containing compound may be included in a reaction mixture in an amount of about 1, 2, 3, 4, 5, 6, 7, 8, 9, 10, 11, 12, 13, 14, 15, 16, 17, 18, 19, or 20 mol %.

d. Ligand

Another starting material in the methods of synthesis described herein is a ligand. The ligand includes at least one atom bearing an unshared electron pair, which may interact with the nickel of the nickel-containing compound. For example, a ligand may include at least one atom selected from nitrogen, phosphorus, arsenic, oxygen, sulfur and carbon that includes an unshared electron pair.

The ligand may be a monodentate ligand, which includes only one atom bearing an unshared electron pair that may interact with the nickel. Exemplary monodentate ligands may include, but are not limited to, monophosphines, such as trialkylphosphines and tricycloalkylphosphines, such as tributylphosphine, tricyclohexylphosphine, and tricyclopentylphosphine. Other exemplary monodentate ligands may include, but are not limited to, N-heterocyclic carbene ligands, such as, for example, 1,3-bis(2,6-diisopropylphenyl) imidazol-2-ylidene (which is often abbreviated Ipr).

In some embodiments, the ligand may be a bidentate or "chelating" ligand, i.e., a ligand comprising two atoms bearing unshared electron pairs, with a spatial relationship therebetween, such that the atoms are capable of interacting simultaneously with the nickel atom or ion. For example, a chelating ligand may be a diamine, aminoalcohol, or a bisphosphine.

A ligand may be included in a reaction mixture in an amount of about 5 mol % to about 30 mol %. For example, a ligand compound may be included in a reaction mixture in an amount of about 5, 6, 7, 8, 9, 10, 11, 12, 13, 14, 15, 16, 17, 18, 19, 20, 21, 22, 23, 24, 25, 26, 27, 28, 29, or 30 mol %. In some embodiments, a ligand may be included in a reaction mixture in an amount of about double the amount of the nickel-containing compound.

Together, the nickel-containing compound and one or more molecules of the ligand may interact to form a metal-ligand complex, which may serve as a catalyst for the reaction.

e. Reaction Conditions

The reaction mixture may further comprise a solvent. Any suitable solvent that is compatible with the components of the reaction mixture may be used. Suitably, a solvent will be selected such that the compounds of formula (II) and (III) will be at least partially soluble (or fully soluble), and will allow the reaction mixture to be heated or cooled to a temperature sufficient for the reaction to produce a compound of formula (I). Exemplary solvents include, but are not limited to: ethers such as diethyl ether, dibutyl ether, 1,2-dimethoxyethane, diglyme, t-butyl methyl ether, tetrahydrofuran, dioxane and the like; halogenated solvents such as chloroform, dichloromethane, dichloroethane, trifluorotoluene, chlorobenzene and the like; aliphatic or aromatic hydrocarbon solvents such as benzene, xylene, toluene, hexane, pentane and the like; esters and ketones such as ethyl acetate, acetone, 2-butanone and the like; polar aprotic solvents such as acetonitrile, dimethylformamide, dimethylsulfoxide and the like; or any combination of two or more solvents. For example, a suitable solvent is toluene.

The reaction may be conducted in a solution in which the concentration of the compound of formula (II) is from about 0.01 M to about 1.0 M, e.g., about 0.01 M, about 0.05 M, about 0.10 M, 0.15 M, 0.20 M, 0.25 M, 0.30 M, 0.35 M, 0.40 M, 0.45 M, 0.50 M, 0.55 M, 0.60 M, 0.65 M, 0.70 M, 0.75 M, 0.80 M, 0.85 M, 0.90 M, 0.95 M, or 1.0 M.

The solvent and/or the reaction mixture may be substantially anhydrous, i.e. may be substantially free of water. In some embodiments, the solvent and/or the reaction mixture may comprise less than about 10 wt. %, 9.5 wt. %, 9.0 wt. %, 8.5 wt. %, 8.0 wt. %, 7.5 wt. %, 7.0 wt. %, 6.5 wt. %, 6.0 wt. %, 5.5 wt. %, 5.0 wt. %, 4.5 wt. %, 4.0 wt. %, 3.5 wt. %, 3.0 wt. %, 2.5 wt. %, 2.0 wt. %, 1.5 wt. %, 1.0 wt. %, 0.95 wt. %, 0.90 wt. %, 0.85 wt. %, 0.80 wt. %, 0.75 wt. %, 0.70 wt. %, 0.65 wt. %, 0.60 wt. %, 0.55 wt. %, 0.50 wt. %, 0.45 wt. %, 0.40 wt. %, 0.35 wt. %, 0.30 wt. %, 0.25 wt. %, 0.20 wt. %, 0.15 wt. %, 0.10 wt. %, 0.09 wt. %, 0.08 wt. %, 0.07 wt. %, 0.06 wt. %, 0.05 wt. %, 0.04 wt. %, 0.03 wt. %, 0.02 wt. % or 0.01 wt. % water.

The method of synthesizing the compound of formula (I) may further comprise cooling the reaction mixture. For example, the reaction mixture may be cooled to a temperature of about −50° C. to about 20° C., about −40° C. to about 15° C., or about −20° C. to about 10° C., e.g., to about −80° C., −75° C., −70° C., −65° C., −60° C., −55° C., −50° C., −45° C., −40° C., −35° C., −30° C., −25° C., −20° C., −15° C., −10° C., −5° C., 0° C., 5° C., 10° C., 15° C., or 20° C. The method of synthesizing the compound of formula (I) may further comprise heating the reaction mixture. For example, the reaction mixture may be heated to a temperature of about 25° C. to about 110° C., e.g., to about 25° C., 30° C., 35° C., 40° C., 45° C., 50° C., 55° C., 60° C., 65° C., 70° C., 75° C., 80° C., 85° C., 90° C., 95° C., 100° C., 105° C., or 110° C.

Other components may also be added to the reaction mixture, such as an acid, a base, or a salt.

The method of synthesizing the compound of formula (I) may further comprise stirring the reaction mixture. For example, the reaction mixture may be stirred using a magnetic stirring bar, or an overhead mixer.

The reaction mixture may be contained within any suitable reaction vessel, such as a vial, flask, beaker, tube (e.g., a sealed tube), or the like. In embodiments, the reaction vessel may be suitably dry, e.g., the reaction vessel may be dried in an oven and/or under vacuum.

The reaction mixture may further comprise an inert atmosphere. For example, a reaction vessel comprising the reaction mixture may consist essentially of an inert gas such as nitrogen, argon, or a mixture thereof. In some embodiments, an inert atmosphere comprises dioxygen ($O_2$) in an amount of less than about 1000 ppm, 900 ppm, 800 ppm, 700 ppm, 600 ppm, 500 ppm, 400 ppm, 300 ppm, 200 ppm, 100 ppm, 95 ppm, 90 ppm, 85 ppm, 80 ppm, 75 ppm, 70 ppm, 65 ppm, 60 ppm, 55 ppm, 50 ppm, 45 ppm, 40 ppm, 35 ppm, 30 ppm, 25 ppm, 20 ppm, 15 ppm, 10 ppm, 9 ppm, 8 ppm, 7 ppm, 6 ppm, 5 ppm, 4 ppm, 3 ppm, 2 ppm or 1 ppm $O_2$.

The method may comprise incubating, stirring and/or heating the reaction mixture for a period of time sufficient to form a compound of formula (I). For example, the reaction mixture may be incubated, stirred and/or heated for about 1 hour to about 24 hours, or about 2 hours to about 12 hours. For example, the reaction mixture may be incubated, stirred and/or heated for about 1, 2, 3, 4, 5, 6, 7, 8, 9, 10, 11, 12, 13, 14, 15, 16, 17, 18, 19, 20, 21, 22, 23, or 24 hours.

The method may provide a compound of formula (I) in a yield of about 20% to about 100%, e.g., about 50% to about 99%. For example, the method may provide a compound of formula (I) in about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% yield.

f. Optional Additional Method Steps

Methods of synthesizing compounds of formula (I) may optionally further include additional process steps. For example, the method may further comprise the step of purifying the compound of formula (I) from the reaction mixture. For example, the reaction mixture may be directly subjected to column chromatography (e.g., flash column chromatography) on a solid phase such as silica gel. The reaction mixture may alternatively be purified using other forms of chromatography, such as high pressure liquid chromatography (HPLC). The reaction mixture may be concentrated or the solvent may be removed prior to purification.

In embodiments in which $R^1$ is a nitrogen protecting group, the method may further comprise the step of removing the nitrogen protecting group. In such methods, the protecting group may be removed using any suitable method that is capable of removing the protecting group. For example, in embodiments in which $R^1$ is a tert-butyloxycarbonyl (Boc) protecting group, the method may further comprise the step of reacting the compound of formula (I) with an acid (e.g., a strong acid such as hydrochloric acid or trifluoroacetic acid). In embodiments in which $R^1$ is a p-toluenesulfonyl (tosyl, Ts) protecting group, the method may further comprise the step of reacting the compound of formula (I) with an acid (e.g., a strong acid such as hydrobromic acid or sulfuric acid), or a reducing agent (e.g., sodium or sodium amalgam).

Following preparation of the compound of formula (I), the carbonyl moiety may be reduced to the alcohol. For example, the method may further comprise the step of reacting the compound of formula (I) with a reducing agent (e.g., sodium borohydride or lithium aluminum hydride), to yield a hydroxylated heterocyclic compound.

g. Product

The product of the reaction is a compound of formula (I) as described above. The product of the reaction may be evaluated using a number of techniques. For example, compounds may be subjected to structural characterization using, for example, nuclear magnetic resonance (NMR) spectroscopy, mass spectrometry (MS), and infrared (IR) spectroscopy. Reactions may be monitored for formation of a product using techniques such as gas chromatography (GC) or thin-layer chromatography (TLC). Purified products may be confirmed using elemental analysis (EA).

In methods for which a compound of formula (III) includes two $R^3$ groups that are different, a reaction may proceed regioselectively. For example, the reaction may produce two products in a ratio of about 99:1 to about 80:20, e.g., about 99.9:0.1, 99:1, 98:2, 97:3, 96:4, 95:5, 94:6, 93:7, 92:8, 91:9, 90:10, 89:11, 8:12, 87:13, 86:14, 85:15, 84:16, 83:17, 82:18, 81:19 or 80:20. Exemplary two products 1 and 2 are illustrated in Scheme 1.

Scheme 1.

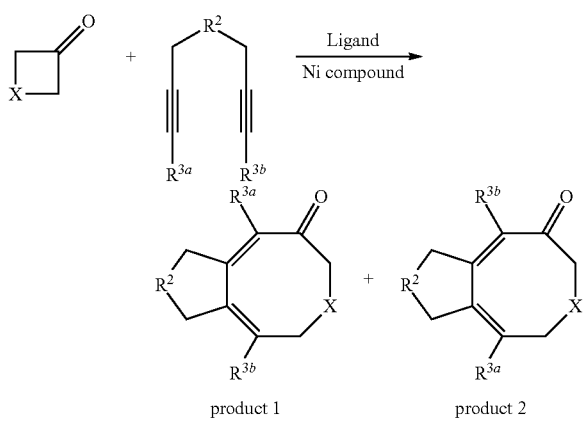

Products 1 and 2 may be separated using techniques known to those skilled in the art, such as chromatography (e.g., column chromatography such as flash column chromatography or HPLC).

3. COMPOUNDS

This disclosure also provides compounds of formula (I), which may be prepared by methods described herein and/or included in pharmaceutical compositions described herein. A compound may have the following formula (I):

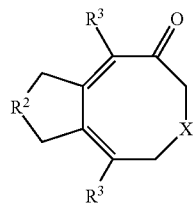

wherein:

X is selected from the group consisting of O and $NR^1$;

$R^1$ is selected from the group consisting of hydrogen, alkyl, and a nitrogen protecting group;

$R^2$ is selected from the group consisting of —C(O)O—, —C(O)—, —O—, —$NR^4$— and —$CR^5_2$—;

each $R^3$ is independently selected from the group consisting of hydrogen, alkyl, alkenyl, alkynyl, cycloalkyl, heterocyclyl, aryl, heteroaryl and cyano, any of which may be optionally substituted;

$R^4$ is selected from the group consisting of hydrogen, alkyl, and a nitrogen protecting group; and each $R^5$ is independently selected from the group consisting of hydrogen, alkyl, alkenyl, alkynyl, cycloalkyl, heterocyclyl, aryl, heteroaryl, acyl, alkoxy, amido, amino, carboxy, cyano, ester, halo, haloalkyl, hydroxy, nitro, phosphonate, sulfinyl, sulfonyl, sulfonate, sulfonamino and sulfonamido, any of which may be optionally substituted; or two $R^5$ are taken together with the atom to which they are attached to form an optionally substituted ring system.

In some embodiments, X is O. In some embodiments, X is $NR^1$. In some embodiments, $R^1$ is alkyl. In some embodiments, $R^1$ is a nitrogen protecting group, such as, e.g., tert-butyloxycarbonyl (Boc) or benzhydryl (Bnh).

In some embodiments, $R^2$ is selected from the group consisting of —O—, —$NR^4$— and —$CR^5_2$—. In some embodiments, $R^2$ is O.

In some embodiments, $R^2$ is —$NR^4$—. In some embodiments, $R^4$ is a nitrogen protecting group, such as, e.g., tert-butyloxycarbonyl (Boc) or tosyl (Ts).

In some embodiments, $R^2$ is —$CR^5_2$—. In some embodiments, the two $R^5$ groups are the same. In some embodiments, the two $R^5$ groups are different.

In some embodiments, each $R^5$ is independently selected from the group consisting of hydrogen, $C_1$-$C_6$ alkyl (e.g., $C_1$-$C_4$ alkyl such as methyl, ethyl, isopropyl, n-propyl and tert-butyl), including substituted $C_1$-$C_6$ alkyl groups (e.g., an alkoxyalkyl group such as methoxymethyl), ester (e.g., a methyl ester or —C(O)OCH$_3$), sulfonyl (e.g., —SO$_2$Ph), aryl (e.g., phenyl), and cyano.

In embodiments, both $R^5$ are taken together with the atom to which they are attached to form an optionally substituted ring. In some embodiments, both $R^5$ are taken together with the atom to which they are attached to form a monocyclic 4-, 5- or 6-membered ring. In some embodiments, two $R^5$ are taken together with the atom to which they are attached to form a ring that is fused to an additional ring, e.g., to make a bicyclic ring system. In some embodiments, both $R^5$ are taken together with the atom to which they are attached to form a ring selected from the group consisting of: a dioxane ring, which may be substituted (e.g., 2,2-dimethyl-1,3-dioxane-4,6-dione); an indane ring, which may be substituted (e.g., 1H-indene-1,3(2H)-dione); an oxetane ring; and an azetidine ring, such as a protected azetidine ring (e.g., 1-benzhydrylazetidine).

a. Salt Forms

Compounds of formula (I) may be in the form of a salt, e.g., a pharmaceutically acceptable salt. The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well-known in the art. The salts may be prepared in situ during the final isolation and purification of the compounds or separately by reacting a compound with a suitable acid or base, depending on the particular substituents found on the compounds described herein. Neutral forms of the compounds may be regenerated by contacting the salt with a base or acid and isolating the parent compound in a conventional manner. The parent form of the compound differs from the various salt forms in certain physical properties, such as solubility in polar solvents, but otherwise the salts are equivalent to the parent form of the compound for the purposes of this disclosure. Examples of pharmaceutically acceptable salts are discussed in Berge et al, 1977, "Pharmaceutically Acceptable Salts." *J. Pharm. Sci.* Vol. 66, pp. 1-19.

Representative acid addition salts may be prepared using various suitable acids for example, including, but are not limited to, acetic, adipic, alginic, citric, aspartic, benzoic, benzenesulfonic, butyric, camphoric, camphorsulfonic, carbonic, digluconic, glycerophosphoric, heptanoic, hexanoic, fumaric, hydrochloric, hydrobromic, hydroiodic, 2-hydroxyethanesulfonic (isethionic), lactic, maleic, methanesulfonic, nicotinic, 2-naphthalenesulfonic, oxalic, pamoic, pectinic, persulfuric, 3-phenylpropionic, picric, pivalic, propionic, succinic, sulfuric, tartaric, thiocyanic, phosphoric, glutamatic, p-toluenesulfonic, and undecanoic acids.

Particular examples of acids which may be employed to form pharmaceutically acceptable acid addition salts include such inorganic acids as hydrochloric acid, hydrobromic acid, sulfuric acid and phosphoric acid and such organic acids as oxalic acid, maleic acid, succinic acid, tartaric acid, and citric acid.

Basic addition salts may be prepared in situ during the final isolation and purification of compounds by reacting a carboxylic acid-containing moiety with a suitable base such as the hydroxide, carbonate or bicarbonate of a pharmaceutically acceptable metal cation or with ammonia or an organic primary, secondary or tertiary amine Pharmaceutically acceptable salts include, but are not limited to, cations based on alkali metals or alkaline earth metals such as lithium, sodium, potassium, calcium, magnesium, and aluminum salts, and the like, and nontoxic quaternary ammonia and amine cations including ammonium, tetramethylammonium, tetraethylammonium, methylamine, dimethylamine, trimethylamine, triethylamine, diethylamine, ethylamine and the such as. Other representative organic amines useful for the formation of base addition salts include ethylenediamine, ethanolamine, diethanolamine, piperidine, and piperazine.

Also, the basic nitrogen-containing groups may be quaternized with such agents as lower alkyl halides such as methyl, ethyl, propyl, and butyl chlorides, bromides and iodides; dialkyl sulfates such as dimethyl, diethyl, dibutyl and diamyl sulfates; long chain halides such as decyl, lauryl, myristyl and stearyl chlorides, bromides and iodides; arylalkyl halides such as benzyl and phenethyl bromides and others. Water or oil-soluble or dispersible products are thereby obtained.

Unless otherwise specified, a reference to a particular compound also includes salt forms thereof b. Isomers Certain compounds may exist in one or more particular geometric, optical, enantiomeric, diastereomeric, epimeric, atropic, stereoisomer, tautomeric, conformational, or anomeric forms, including but not limited to, cis- and trans-forms; E- and Z-forms; c-, t-, and r-forms; endo- and exo-forms; R-, S-, and meso-forms; D- and L-forms; d- and l-forms; (+) and (−) forms; keto-, enol-, and enolate-forms; syn- and anti-forms; synclinal- and anticlinal-forms; a- and β-forms; axial and equatorial forms; boat-, chair-, twist-, envelope-, and half chair-forms; and combinations thereof, hereinafter collectively referred to as "isomers" (or "isomeric forms").

In one embodiment, a compound described herein may be an enantiomerically enriched isomer of a stereoisomer described herein, or a method of synthesizing a compound may produce an enantiomerically enriched isomer of a stereoisomer described herein. For example, the compound may have an enantiomeric excess of at least about 10%, 15%, 20%, 25%, 30%, 35%, 40%, 45%, 50%, 55%, 60%, 65%, 70%, 75%, 80%, 85%, 90%, 95%, 96%, 97%, 98%, or 99%. Enantiomer, when used herein, refers to either of a pair of chemical compounds whose molecular structures have a mirror-image relationship to each other.

In one embodiment, a preparation of a compound disclosed herein is enriched for an isomer of the compound having a selected stereochemistry, e.g., R or S, corresponding to a selected stereocenter. For example, the compound has a purity corresponding to a compound having a selected stereochemistry of a selected stereocenter of at least about 60%, 65%, 70%, 75%, 80%, 85%, 90%, 95%, 96%, 97%, 98%, or 99%.

In one embodiment, a composition described herein includes a preparation of a compound disclosed herein that is enriched for a structure or structures having a selected stereochemistry, e.g., R or S, at a selected stereocenter. Exemplary R/S configurations may be those provided in an example described herein.

An "enriched preparation," as used herein, is enriched for a selected stereoconfiguration of one, two, three or more selected stereocenters within the subject compound. Exemplary selected stereocenters and exemplary stereoconfigurations thereof may be selected from those provided herein, e.g., in an example described herein. By enriched is meant at least 60%, e.g., of the molecules of compound in the preparation have a selected stereochemistry of a selected stereocenter. In an embodiment it is at least 65%, 70%, 75%, 80%, 85%, 90%, 95%, 96%, 97%, 98%, or 99%. Enriched refers to the level of a subject molecule(s) and does not connote a process limitation unless specified.

Compounds may be prepared in racemic form or as individual enantiomers or diastereomers by either stereospecific synthesis or by resolution. The compounds may, for example, be resolved into their component enantiomers or diastereomers by standard techniques, such as the formation of stereoisomeric pairs by salt formation with an optically active base, followed by fractional crystallization and regeneration of the free acid. The compounds may also be resolved by formation of stereoisomeric esters or amides, followed by chromatographic separation and removal of the chiral auxiliary. Alternatively, the compounds may be resolved using a chiral HPLC column. The enantiomers also may be obtained from kinetic resolution of the racemate of corresponding esters using lipase enzymes.

Except as discussed below for tautomeric forms, specifically excluded from the term "isomers," as used herein, are structural (or constitutional) isomers (i.e., isomers which differ in the connections between atoms rather than merely by the position of atoms in space). For example, a reference to a methoxy group, —$OCH_3$, is not to be construed as a reference to its structural isomer, a hydroxymethyl group, —$CH_2OH$. Similarly, a reference to ortho-chlorophenyl is not to be construed as a reference to its structural isomer, meta-chlorophenyl. However, a reference to a class of structures may well include structurally isomeric forms falling within that class (e.g., $C_3$-alkyl or propyl includes n-propyl and iso-propyl; $C_4$-alkyl or butyl includes n-, iso-, sec-, and tert-butyl; methoxyphenyl includes ortho-, meta-, and para-methoxyphenyl).

The above exclusion does not pertain to tautomeric forms, for example, keto-, enol-, and enolate-forms, as in, for example, the following tautomeric pairs: keto/enol, imine/enamine, amide/imino alcohol, amidine/amidine, nitroso/oxime, thioketone/enethiol, N-nitroso/hydroxyazo, and nitro/aci-nitro.

Note that specifically included in the term "isomer" are compounds with one or more isotopic substitutions. For example, H may be in any isotopic form, including $^1H$, $^2H$ (D), and $^3H$ (T); C may be in any isotopic form, including $^{12}C$, $^{13}C$, and $^{14}C$; O may be in any isotopic form, including $^{16}O$ and $^{18}O$; and the like.

3. PHARMACEUTICAL COMPOSITIONS

The disclosure also provides pharmaceutical compositions comprising a compound of formula (I), and a pharmaceutically acceptable carrier. The term "pharmaceutically acceptable carrier," as used herein, means a non-toxic, inert solid, semi-solid or liquid filler, diluent, encapsulating material or formulation auxiliary of any type. Some examples of materials which may serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; cocoa butter and suppository waxes; oils such as peanut oil, cottonseed oil, safflower oil, sesame oil, olive oil, corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants may also be present in the composition, according to the judgment of one skilled in the art of formulations.

The pharmaceutical compositions may be administered to subjects (e.g., humans and other mammals) orally, rectally, parenterally, intracisternally, intravaginally, intraperitoneally, topically (as by powders, ointments or drops), bucally or as an oral or nasal spray. The term "parenterally," as used herein, refers to modes of administration, including intravenous, intramuscular, intraperitoneal, intrasternal, subcutaneous, intraarticular injection and infusion.

Pharmaceutical compositions for parenteral injection comprise pharmaceutically acceptable sterile aqueous or non-aqueous solutions, dispersions, suspensions or emulsions and sterile powders for reconstitution into sterile injectable solutions or dispersions. Examples of suitable aqueous and non-aqueous carriers, diluents, solvents or vehicles include water, ethanol, polyols (propylene glycol, polyethylene glycol, glycerol, and the like, and suitable mixtures thereof), vegetable oils (such as olive oil) and injectable organic esters such as ethyl oleate, or suitable mixtures thereof. Suitable fluidity of the composition may be maintained, for example, by the use of a coating such as lecithin, by the maintenance of the required particle size in the case of dispersions, and by the use of surfactants.

These compositions may also contain adjuvants such as preservative agents, wetting agents, emulsifying agents, and dispersing agents. Prevention of the action of microorganisms may be ensured by various antibacterial and antifungal agents, for example, parabens, chlorobutanol, phenol, sorbic acid, and the like. It also may be desirable to include isotonic agents, for example, sugars, sodium chloride and the like. Prolonged absorption of the injectable pharmaceutical form may be brought about by the use of agents delaying absorption, for example, aluminum monostearate and gelatin.

In some cases, in order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug may depend upon its rate of dissolution, which, in turn, may depend upon crystal size and crystalline form. Alternatively, a parenterally administered drug form may be administered by dissolving or suspending the drug in an oil vehicle.

Suspensions, in addition to the active compounds, may contain suspending agents, for example, ethoxylated isostearyl alcohols, polyoxyethylene sorbitol and sorbitan esters, microcrystalline cellulose, aluminum metahydroxide, bentonite, agar-agar, tragacanth, and mixtures thereof.

If desired, and for more effective distribution, the compounds may be incorporated into slow-release or targeted-delivery systems such as polymer matrices, liposomes, and microspheres. They may be sterilized, for example, by filtration through a bacteria-retaining filter or by incorporation of sterilizing agents in the form of sterile solid compositions, which may be dissolved in sterile water or some other sterile injectable medium immediately before use.

Injectable depot forms are made by forming microencapsulated matrices of the drug in biodegradable polymers such as polylactide-polyglycolide. Depending upon the ratio of drug to polymer and the nature of the particular polymer employed, the rate of drug release may be controlled. Examples of other biodegradable polymers include poly(orthoesters) and poly(anhydrides) Depot injectable formulations also are prepared by entrapping the drug in liposomes or microemulsions which are compatible with body tissues.

The injectable formulations may be sterilized, for example, by filtration through a bacterial-retaining filter or by incorporating sterilizing agents in the form of sterile solid compositions which may be dissolved or dispersed in sterile water or other sterile injectable medium just prior to use.

Injectable preparations, for example, sterile injectable aqueous or oleaginous suspensions may be formulated according to the known art using suitable dispersing or wetting agents and suspending agents. The sterile injectable preparation also may be a sterile injectable solution, suspension or emulsion in a nontoxic, parenterally acceptable diluent or solvent such as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid are used in the preparation of injectables.

Solid dosage forms for oral administration include capsules, tablets, pills, powders, and granules. In such solid dosage forms, one or more compounds is mixed with at least one inert pharmaceutically acceptable carrier such as sodium citrate or dicalcium phosphate and/or a) fillers or extenders such as starches, lactose, sucrose, glucose, mannitol, and salicylic acid; b) binders such as carboxymethylcellulose, alginates, gelatin, polyvinylpyrrolidinone, sucrose, and acacia; c) humectants such as glycerol; d) disintegrating agents such as agar-agar, calcium carbonate, potato or tapioca starch, alginic acid, certain silicates, and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay; and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using lactose or milk sugar as well as high molecular weight polyethylene glycols.

The solid dosage forms of tablets, dragees, capsules, pills, and granules may be prepared with coatings and shells such as enteric coatings and other coatings well-known in the pharmaceutical formulating art. They may optionally contain opacifying agents and may also be of a composition that they release the active ingredient(s) only, or preferentially, in a certain part of the intestinal tract in a delayed manner. Examples of materials useful for delaying release of the active agent may include polymeric substances and waxes.

Compositions for rectal or vaginal administration are preferably suppositories which may be prepared by mixing the compounds with suitable non-irritating carriers such as cocoa butter, polyethylene glycol or a suppository wax which are solid at ambient temperature but liquid at body temperature and therefore melt in the rectum or vaginal cavity and release the active compound.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions may also include adjuvants such as wetting agents, emulsifying and suspending agents, sweetening, flavoring, and perfuming agents.

Suspensions, in addition to the active compounds, may contain suspending agents, for example, ethoxylated isostearyl alcohols, polyoxyethylene sorbitol and sorbitan esters, microcrystalline cellulose, aluminum metahydroxide, bentonite, agar-agar, tragacanth, and mixtures thereof.

If desired, and for more effective distribution, the compounds may be incorporated into slow-release or targeted-delivery systems such as polymer matrices, liposomes, and microspheres. They may be sterilized, for example, by filtration through a bacteria-retaining filter or by incorporation of sterilizing agents in the form of sterile solid compositions, which may be dissolved in sterile water or some other sterile injectable medium immediately before use.

Dosage forms for topical or transdermal administration of a compound include ointments, pastes, creams, lotions, gels, powders, solutions, sprays, inhalants or patches. A desired compound is admixed under sterile conditions with a pharmaceutically acceptable carrier and any needed preservatives or buffers as may be required. Ophthalmic formulation, eardrops, eye ointments, powders and solutions are also contemplated as being within the scope of this disclosure.

The ointments, pastes, creams and gels may contain, in addition to an active compound, animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays may contain, in addition to the compounds, lactose, talc, silicic acid, aluminum hydroxide, calcium silicates and polyamide powder, or mixtures of these substances. Sprays may additionally contain customary propellants such as chlorofluorohydrocarbons.

Compounds also may be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes may be used. The present compositions in liposome form may contain, in addition to the compounds, stabilizers, preservatives, and the like. The preferred lipids are the natural and synthetic phospholipids and phosphatidylcholines (lecithins) used separately or together. Methods to form liposomes are known in the art. See, for example, Prescott, Ed., Methods in Cell Biology, Volume XIV, Academic Press, New York, N.Y., (1976), p 33 et seq.

Dosage forms for topical administration of a compound described herein include powders, sprays, ointments and inhalants. The active compound is mixed under sterile conditions with a pharmaceutically acceptable carrier and any needed preservatives, buffers or propellants. Ophthalmic formulations, eye ointments, powders and solutions are also contemplated as being within the scope of this disclosure. Aqueous liquid compositions may also be useful.

It will be readily apparent to those skilled in the art that other suitable modifications and adaptations of the compounds and methods of the present disclosure described herein are readily applicable and appreciable, and may be made using suitable equivalents without departing from the scope of the present disclosure or the aspects and embodiments disclosed herein. Having now described the present disclosure in detail, the same will be more clearly understood by reference to the following examples which are merely intended only to illustrate some aspects and embodiments of the disclosure, and should not be viewed as limiting to the scope of the disclosure. The disclosures of all journal references, U.S. patents and publications referred to herein are hereby incorporated by reference in their entireties.

EXAMPLES

General Experimental and Analytical Details

All reactions were conducted under an atmosphere of $N_2$ using standard Schlenk techniques or in a $N_2$ filled glove-box unless otherwise noted. Toluene was dried over neutral alumina under $N_2$ using a Grubbs type solvent purification system. Ni(cod)$_2$ was purchased from Strem and used without further purification. 3-Boc-azetidinone 2a, and 3-benzhydryl-azetidinone 2d were purchased from Sigma-Aldrich and Synthonix respectively, and used as received. Diynes 1a, 1c, 1d, 1e, 1i, 1l, and 1n were prepared according to reported procedures (Kumar et al. *J. Am. Chem. Soc.* 2011, 133, 7719; Louie et al. *J. Am. Chem. Soc.* 2002, 124, 15188; Duong et al. *J. Am. Chem. Soc.* 2004, 126, 11438; Kumar et al. *Angew. Chem. Int. Ed.* 2011, 50, 10694). Diynes 1b, 1f, and 1m were prepared according to reported procedures (Zhang et al. *J. Org. Chem.* 2011, 76, 4686). Diynes 1g (Hashmi, A. S. K.; Häffner, T.; Rudolph, M.; Rominger, F. *Chem. Eur. J.* 2011, 17, 8195), 1 h (Sperger, C. A.; Fiksdahl, A. *J. Org. Chem.* 2010, 75, 4542), 1j (the diyne (1) was converted to diol which was transformed to oxetane using the protocol in Loy et al. *J. Am. Chem. Soc.* 2009, 131, 2786), 1k (the diol of (1) was converted to azetidine using the procedure in Hillier et al. *J. Org. Chem.* 2006, 71, 7885), and 1o (McDonald et al. *J. Am. Chem. Soc.* 1995, 117, 6605) were also prepared according to reported procedures. All other reagents were purchased from commercial suppliers and used without further purification unless otherwise noted.

$^1$H and $^{13}$C Nuclear Magnetic Resonance spectra of pure compounds were acquired at 300, 400, 500 and 100, 125 MHz, respectively unless otherwise noted. All spectra are referenced to a singlet at 7.27 ppm for $^1$H and to the center line of a triplet at 77.23 ppm for $^{13}$C. The abbreviations s, d, dd, dt, dq, t, q, and quint stand for singlet, doublet, doublet of doublets, doublet of triplets, doublet of quartets, triplet, quartet, and quintet, in that order. All $^{13}$C NMR spectra were proton decoupled. IR spectra were recorded on a Bruker Tensor 27 FT-IR spectrometer.

Example 1

Reaction Screening

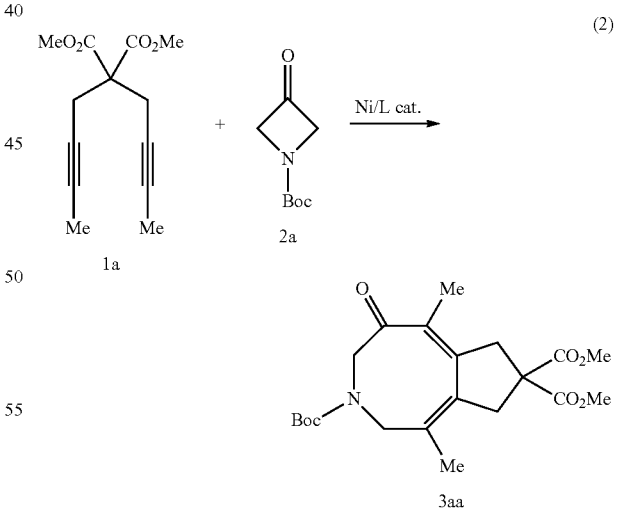

Using Ni(cod)$_2$ as the catalyst, various ligands were screened for coupling diyne 1a and azetidinone 2a. Results and specific reaction conditions are shown in Table 1. Under the indicated reaction conditions, the three cases where some desired product was formed was when electron-donating phosphines were used (i.e., P(n-Bu)$_3$, PCy$_3$, and P(Cyp)$_3$, entries 5-7 respectively).

TABLE 1

Ligand evaluation for the Ni-catalyzed coupling of diyne 1a and azetidinone 2a[a]

| entry | ligand | 2a conversion[b] | 3aa isolated yield |
|---|---|---|---|
| 1 | PPh$_3$ | 49% | n.d.[c] |
| 2 | DPPF | 48% | n.d.[c] |
| 3 | BINAP | — | n.d.[c] |
| 4 | PCy$_2$Ph | 60% | n.d.[c] |
| 5 | P(n-Bu)$_3$ | 72% | 23% |
| 6 | PCy$_3$ | 83% | 37% (28%)[d] |
| 7 | PCyp$_3$ | 81% | 30% |
| 8 | 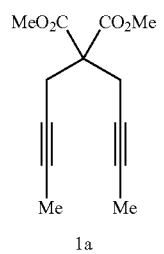 | 18% | n.d.[c] |
| 9 | IPr | >99% | 70%[e] |

[a]Azetidinone 2a (0.1M), diyne 1a (0.12M), 10 mol % Ni(cod)$_2$, L (20 mol % for entry 1, 4-8 and 10 mol % for entries 2-3), toluene, 100° C., 12 h.
[b]Conversion of diyne was determined by $^1$H NMR using 1. 3,5-trimethoxybenzene as an internal standard.
[c]n.d. = not detected.
[d]Diyne 1a was added dropwise to the reaction mixture.
[e]Reaction was run at rt.

Using the N-heterocyclic carbene (NHC) ligand, Ipr, proved to be advantageous as product 3aa was formed at rt in 70% yield. Further screening of reaction temperatures and concentrations were performed using this ligand. Results are illustrated in Table 2, which also shows the reaction conditions.

TABLE 2

Temperature effect evaluation on the Ni/IPr-catalyzed coupling of 1a and 2a to afford 3aa[a]

| entry | temperature | a concentration | 1a isolated yield |
|---|---|---|---|
| 1 | rt | 0.1M | 70% |
| 2 | 60° C. | 0.1M | 35% |
| 3 | 100° C. | 0.1M | 21% |
| 4 | 0° C. | 0.1M | 84% |
| 5 | 0° C. | 0.2M | 68% |
| 6 | 0° C. | 0.05M | 88% |

[a]Azetidinone 2a (0.1M), diyne 1a (0.12M), 10 mol % Ni(cod)$_2$, 20 mol % IPr, toluene, 8 h.

Various N-protecting groups on the azetidinone were also screened. Results are illustrated in Scheme 2, with the reaction conditions also indicated. The Boc and Bnh protecting groups provided the greatest yields under these reaction conditions.

Scheme 2.

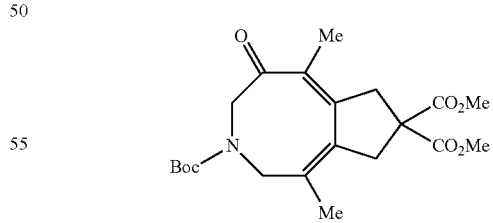

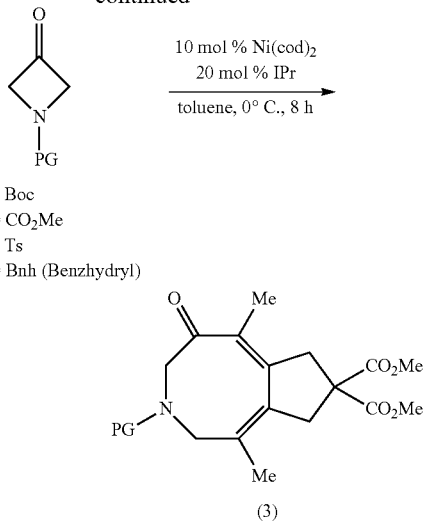

2a PG = Boc
2b PG = CO$_2$Me
2c PG = Ts
2d PG = Bnh (Benzhydryl)

3aa, 88%
3ab, 69%
3ac, 25%
3ad, 92%

Example 2

Compound Synthesis

General Procedure

In a nitrogen filled glovebox, a scintillation vial equipped with a magnetic stir bar was charged with the appropriate diyne (1.2 equiv) and the appropriate azetidinone (1 equiv, 0.05 M). To this mixture in toluene was added catalyst solution which was prepared in toluene by mixing Ni(cod)$_2$ and 1,3-bis(2,6-diisopropylphenyl)imidazol-2-ylidene (Ipr) in 1:2 molar ratio (The stock catalyst solution was allowed to stir for at least 6 h before use). The reaction was immediately brought outside of the glove box, sealed and stirred at 0° C. for 8 h. The solvent was removed under vacuum and the product was purified by silica gel flash column chromatography.

(1Z,6Z)-3-Tert-butyl 8,8-dimethyl 1,6-dimethyl-5-oxo-4,5-dihydro-2H-cyclopenta[d]azocine-3,8,8(7H,9H)-tricarboxylate (3aa)

The general procedure for cycloaddition was used with diyne 1a (16.6 mg, 0.07 mmol), N-Boc azetidinone 2a (10 mg, 0.05 mmol). The crude product was purified by flash column chromatography on silica gel (50% diethyl ether in pentane or 30% EtOAc in hexanes) to afford the azocine 3aa as pale yellow oil, in 88% yield. $^1$H NMR (400 MHz, CDCl$_3$): δ (ppm) 4.00 (s, 2H), 3.87 (s, 2H), 3.76 (s, 6H), 3.17 (s, 2H), 3.14 (s, 2H), 1.94 (s, 3H), 1.92 (s, 3H), 1.46 (s, 9H). $^{13}$C NMR (100 MHz, CDCl$_3$): δ (ppm) 171.6, 55.8, 53.4, 41.6, 39.1, 28.5, 16.4 (Please note that due to the presence of Boc-group some peaks were missing in $^{13}$C NMR acquired at about 20° C. To address this issue, deprotection of Boc-group was performed which afforded 3aa' (for Boc deprotection procedure and full characterization of 3aa', see next entry). IR (CH$_2$Cl$_2$, cm$^{-1}$): 2977, 1735, 1695, 1435, 1368, 1251, 1205, 1159, 1070. HRMS (ESI) calcd for C$_{21}$H$_{29}$NO$_2$Na [M+Na]+ 430.1842. found 430.1847.

(1Z,6Z)-dimethyl 1,6-dimethyl-5-oxo-4,5,7,9-tetrahydro-2H-cyclopenta[d]azocine-8,8(3H)-dicarboxylate (3aa')

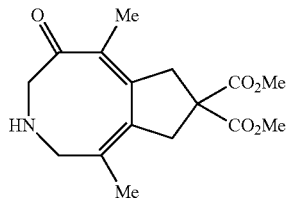 [SMILES: COC(=O)C1(C(=O)OC)CC2=C(\C)CNCC(=O)/C(C)=C\2C1]

To a solution of 3aa (8 mg, 0.01 mmol, 0.1 M) in DCM (0.18 ml), trifluoroacetic acid was added (20.4 mg, 0.18 mmol, 0.013 ml). The reaction mixture was stirred at room temperature for 5 h. The solvent was removed under vacuum. The residue was diluted by dichloromethane (1 ml) and washed with saturated aqueous K$_2$CO$_3$ solution. The organic phase was dried by Na$_2$SO$_4$ and solvent was removed under vacuum to yield 3aa' in 90% as an orange oil. $^1$H NMR (500 MHz, CDCl$_3$): δ (ppm) 3.89 (br, 2H), 3.77 (s, 6H), 3.71 (bs, 3H), 3.23 (s, 2H), 3.21 (s, 2H), 2.10 (s, 3H), 1.95 (s, 3H). $^{13}$C NMR (125 MHz, CDCl$_3$): δ (ppm) 194.1, 171.3, 150.9, 142.9, 134.4, 131.9, 55.7, 53.6, 48.8, 48.2, 42.0, 39.4, 21.8, 16.2. IR (CH$_2$Cl$_2$, cm$^{-1}$): 2960, 1737, 1676, 1438, 1273, 1206. HRMS (ESI) calcd for C$_{16}$H$_{22}$NO$_5$ [M]$^+$ 308.1498. found 308.1500.

(1Z,6Z)-Trimethyl 1,6-dimethyl-5-oxo-4,5-dihydro-2H-cyclopenta[d]azocine-3,8,8(7H,9H)-tricarboxylate (3ab)

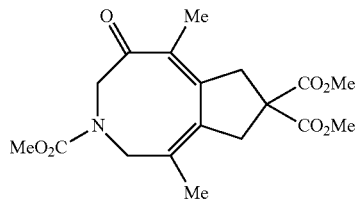 [SMILES: COC(=O)N1CC(=O)/C(C)=C2/CC(C(=O)OC)(C(=O)OC)C/C2=C(\C)C1]

The general procedure for cycloaddition was used with diyne 1a (22.0 mg, 0.92 mmol), azetidinone 2b (9.1 mg, 0.07 mmol). The crude reaction mixture was purified by flash column chromatography on silica gel (60% diethyl ether in pentane) to afford the azocine 3ab as light yellow oil, in 69% yield. $^1$H NMR (400 MHz, CDCl$_3$): δ (ppm) 4.07-4.11 (br, 1H), 4.03-4.07 (br, 2H), 3.89-3.94 (br, 1H), 3.84-3.89 (br, 1H), 3.75 (s, 6H), 3.71 (s, 3H), 3.19 (s, 2H), 3.16 (s, 2H), 1.96 (s, 3H), 1.92 (s, 3H). $^{13}$C NMR (400 MHz, CDCl$_3$): δ (ppm) 197.6, 171.7, 156.5, 149.2, 137.7, 134.5, 133.8, 55.9, 53.5, 53.4, 51.0, 49.4, 41.8, 39.1, 21.6, 16.3. IR (CH$_2$Cl$_2$, cm$^{-1}$): 2956, 1737, 1704, 1654, 1444, 1402, 1233, 1202, 1069. HRMS (ESI) calcd for C$_{18}$H$_{23}$NO$_7$ [M+H]+ 366.1553. found 366.1546.

(1Z,6Z)-Dimethyl 1,6-dimethyl-5-oxo-3-tosyl-4,5,7,9-tetrahydro-2H-cyclopenta[d]azocine-8,8(3H)-dicarboxylate (3ac)

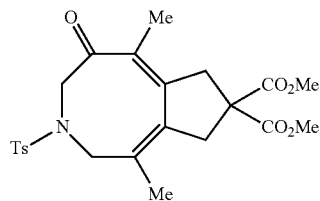 [SMILES: COC(=O)C1(C(=O)OC)CC2=C(\C)CN(S(=O)(=O)c3ccc(C)cc3)CC(=O)/C(C)=C\2C1]

The general procedure for cycloaddition was used with diyne 1a (18.9 mg, 0.08 mmol), 3-azetidinone 2c (14.8 mg, 0.06 mmol). The crude reaction mixture was purified by flash column chromatography on silica gel (50% diethyl ether in pentane or 30% EtOAc in hexanes) to afford the azocine 3ac as pale yellow oil, in 25% yield. $^1$H NMR (500 MHz, CDCl$_3$): δ (ppm) 7.74 (d, J=8.5 Hz, 2H), 7.30 (d, J=8.5 Hz, 2H), 4.01 (s, 2H), 3.75 (s, 6H), 3.64 (s, 2H), 3.17 (s, 2H), 3.13 (s, 2H), 2.41 (s, 3H), 2.05 (s, 3H), 1.78 (s, 3H). $^{13}$C NMR (500 MHz, CDCl$_3$): δ (ppm) 195.2, 171.6, 149.5, 143.8, 138.9, 136.2, 134.7, 133.8, 129.8, 128.2, 55.8, 53.6, 51.7, 50.3, 41.9, 39.1, 21.9, 21.2, 16.2. IR (CH$_2$Cl$_2$, cm$^{-1}$): 2955, 1735, 1652, 1436, 1349, 1257, 1159, 1087, 1027, 720. HRMS (ESI) calcd for C$_{23}$H$_{27}$NO$_7$NaS [M+Na]+ 484.1406. found 484.1407.

(1Z,6Z)-dimethyl 3-benzhydryl-1,6-dimethyl-5-oxo-4,5,7,9-tetrahydro-2H-Cyclopenta[d]azocine-8,8(3H)-dicarboxylate (3ad)

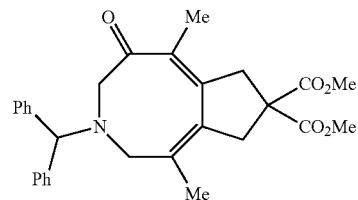 [SMILES: COC(=O)C1(C(=O)OC)CC2=C(\C)CN(C(c3ccccc3)c3ccccc3)CC(=O)/C(C)=C\2C1]

The general procedure for cycloaddition reaction was used with diyne 1a 27.83 mg, 0.11 mmol), azetidinone 2d (23.3 mg, 0.09 mmol). The crude reaction mixture was purified by flash column chromatography on silica gel (25% diethyl ether in pentane or 15% EtOAc in hexanes) to afford the azocine 3ad as pale yellow solid in 92% yield. Mp: 50-52° C. $^1$H NMR (400 MHz, CDCl$_3$): δ (ppm) 7.47 (d, J=7.2 Hz, 4H), 7.26-7.21 (t, J=7.2 Hz, 4H), 7.12 (t, J=7.4 Hz, 2H), 4.66 (s, 1H), 3.70 (s, 6H), 3.30-3.44 (br, 1H), 3.15 (s, 4H), 2.87 (s, 2H), 1.98 (d, 3H), 1.86 (s, 3H). $^{13}$C NMR (400 MHz, CDCl$_3$): δ (ppm) 202.9, 171.8, 148.8, 143.7, 137.7, 137.5, 134.5, 128.9, 128.1, 127.3, 73.8, 56.3, 55.3, 54.4, 53.4, 41.9, 39.3, 22.0, 15.8. IR (CH$_2$Cl$_2$, cm$^{-1}$): 2954, 1734, 1635, 1559, 1453, 1435, 1264, 1204, 1069, 732, 704. HRMS (ESI) calcd for C$_{29}$H$_{32}$NO$_5$ [M+H]+ 474.2280. found 474.2287.

(1Z,6Z)-tert-butyl 1,2',2',6-tetramethyl-4',5,6'-trioxo-4,5,7,9-tetrahydrospiro[cyclopenta[d]azocine-8,5'-[1,3]dioxane]-3(2H)-carboxylate (3bd)

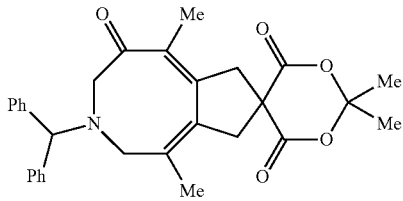 [SMILES: C/C1=C2\CC3(C\C2=C(/C)C(=O)CN(C(c2ccccc2)c2ccccc2)C1)C(=O)OC(C)(C)OC3=O]

The general procedure was used with diyne 1b (24.1 mg, 0.09 mmol), azetidinone 2d (19.2 mg, 0.08 mmol). The crude reaction mixture was purified by flash column chromatography on silica gel (60% diethyl ether in pentane or 30% EtOAc in hexanes) to afford the azocine 3bd as a slightly yellow solid in 78% yield. Mp: 148-150° C. $^1$H NMR (400 MHz, CDCl$_3$): δ (ppm) 7.52 (d, J=7.2 Hz, 4H), 7.28 (t, J=7.2 Hz, 4H), 7.17 (t, J=7.2 Hz, 2H), 4.72 (s, 1H), 3.48 (br, 2H), 3.26 (s, 2H), 3.23 (s, 2H), 2.99 (s, 2H), 2.01 (s, 3H), 1.89 (s, 3H), 1.81 (s, 3H), 1.79 (s, 3H). $^{13}$C NMR (400 MHz, CDCl$_3$): δ (ppm) 202.7, 170.4, 147.6, 143.5, 138.0, 136.4, 134.2, 128.8, 128.0, 127.2, 105.4, 73.7, 55.4, 54.2, 49.6, 45.3, 43.5, 29.2, 29.1, 22.1, 15.8. IR (CH$_2$Cl$_2$, cm$^{-1}$): 2924, 1775, 1742, 1641, 1453, 1391, 1301, 1206, 1045. HRMS (ESI) calcd for C$_{30}$H$_{32}$NO$_5$ [M+H]+ 486.2280. found 486.2281.

(1Z,6Z)-3-Benzhydryl-8,8-bis((benzyloxy)methyl)-1,6-dimethyl-3,4,8,9-tetrahydro-2H-cyclopenta[d]azocin-5(7H)-one (3cd)

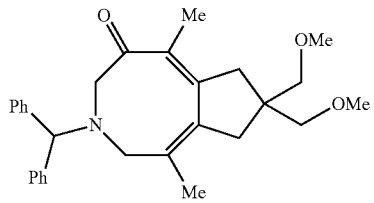 [SMILES: COCC1(COC)CC2=C(\C)CN(C(c3ccccc3)c3ccccc3)CC(=O)/C(C)=C\2C1]

The general procedure was used with diyne 1c (12.6 mg, 0.06 mmol), azetidinone 2d (12.0 mg, 0.05 mmol). The crude reaction mixture was purified by flash column chromatography on silica gel (30% diethyl ether in pentane) to afford the azocine 3cd as a pale yellow oil in 48% yield. $^1$H NMR (400 MHz, CDCl$_3$): δ (ppm) 7.51 (d, 4H), 7.26 (t, 4H), 7.14 (t, 2H), 4.69 (s, 1H), 3.32 (s, 7H), 3.23 (s, 5H), 2.91 (s, 2H), 2.47 (s, 2H), 2.45 (s, 2H), 1.98 (s, 3H), 1.86 (s, 3H). $^{13}$C NMR (400 MHz, CDCl$_3$): δ (ppm) 203.0, 152.5, 143.9, 140.3, 134.4, 128.9, 128.2, 127.3, 76.2, 73.8, 59.7, 43.7, 40.8, 37.6, 22.1, 15.8. IR (CH$_2$Cl$_2$, cm$^{-1}$): 2924, 2886, 2824, 1727, 1635, 1586, 1453, 1375, 1336, 1304, 1282, 1111, 1043. HRMS (ESI) calcd for C$_{29}$H$_{36}$NO$_3$ [M+H]+ 466.2690. found 446.2687.

(3aE,9E)-6-Benzhydryl-4,9-dimethyl-3,5,6,7-tetrahydrofuro[3,4-d]azocin-8(1H)-one (3dd)

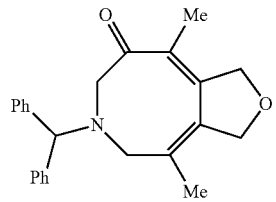 [SMILES: C/C1=C2\COC\C2=C(/C)C(=O)CN(C(c2ccccc2)c2ccccc2)C1]

The general procedure was used with diyne 1d (12.4 mg, 0.10 mmol), azetidinone 2d (20.1 mg, 0.08 mmol). The crude reaction mixture was purified by flash column chromatography on silica gel (30% diethyl ether in pentane or 15% EtOAc in hexanes) to afford the azocine 3dd as a yellow solid in 91% yield. Mp: 124-126° C. $^1$H NMR (400 MHz, CDCl$_3$): δ (ppm) 7.51 (d, J=7.6 Hz, 4H), 7.28 (t, J=7.2 Hz, 4H), 7.17 (t, J=7.2 Hz, 2H), 4.75 (s, 1H), 4.65 (s, 2H), 4.60 (s, 2H), 3.45 (s, 2H), 2.99 (s, 2H), 1.97 (s, 3H), 1.81 (s, 3H). $^{13}$C NMR (400 MHz, CDCl$_3$): δ (ppm) 203.7, 147.4, 143.4, 137.1, 136.7, 131.8, 128.8, 128.0, 127.3, 73.8, 73.2, 71.9, 55.5, 54.5, 22.1, 15.1. IR (CH$_2$Cl$_2$, cm$^{-1}$): 2843, 1644, 1601, 1492, 1453, 1049. HRMS (ESI) calcd for C$_{24}$H$_{25}$NO$_2$Na [M+Na]+ 382.1783. found 382.1796.

The crystals suitable for single crystal X-ray crystallography were grown from slow diffusion of hexanes into a saturated solution of 3dd in THF.

(3aE,9E)-6-Benzhydryl-4,9-dimethyl-2-tosyl-2,3,6,7-tetrahydro-1H-pyrrolo[3,4-d]azocin-8(5H)-one (3ed)

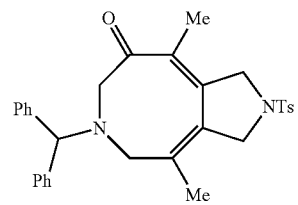 [SMILES: C/C1=C2\CN(S(=O)(=O)c3ccc(C)cc3)C\C2=C(/C)C(=O)CN(C(c2ccccc2)c2ccccc2)C1]

The general procedure was used with diyne 1e (26.59 mg, 0.09 mmol), azetidinone 2d (19.1 mg, 0.08 mmol). The crude reaction mixture was purified by flash column chromatography on silica gel (30% diethyl ether in pentane or 15-20% EtOAc in hexanes) to afford the azocine 3ed as a yellow solid in 79% yield. Mp: 122-124° C. $^1$H NMR (500 MHz, CDCl$_3$): δ (ppm) 7.73 (d, J=8.5 Hz, 2H), 7.47 (d, J=7.5 Hz, 2H), 7.31 (d, J=9 Hz, 2H), 7.27 (t, J=7.5 Hz, 4H), 7.16 (t, J=7.0 Hz, 2H), 4.66 (s, 1H), 4.15 (s, 2H), 4.11 (s, 2H), 3.24-3.31 (br, 2H), 2.83 (s, 2H), 2.37 (s, 3H), 1.95 (s, 3H), 1.81 (s, 3H). $^{13}$C NMR (500 MHz, CDCl$_3$): δ (ppm) 202.9, 144.3, 144.1, 143.2, 138.7, 134.1, 133.8, 133.3, 130.1, 128.9, 127.9, 127.3, 73.7, 55.0, 54.2, 53.8, 52.0, 22.2, 21.7, 15.5. IR (CH$_2$Cl$_2$, cm$^{-1}$): 3029, 2925, 2853, 1644, 1597, 1452, 1347, 1163, 1095, 1044. HRMS (ESI) calcd for C$_{31}$H$_{32}$N$_2$O$_3$SNa [M+Na]+ 535.2031. found 535.2044.

(1Z,6Z)-3-Benzhydryl-1,6-dimethyl-8,8-bis(phenylsulfonyl)-3,4,8,9-tetrahydro-2H-cyclopenta[d]azocin-5(7H)-one (3fd)

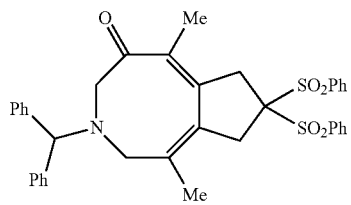

The general procedure was used with diyne 1f (36.6 mg, 0.09 mmol), azetidinone 2d (18.1 mg, 0.07 mmol). The crude reaction mixture was purified by flash column chromatography on silica gel (50% diethyl ether in pentane or 30% EtOAc in hexanes) to afford the azocine 3fd as a yellow solid in 59%. Mp=192° C. (Decomp). $^1$H NMR (400 MHz, CDCl$_3$): δ (ppm) 7.99 (d, J=7.2 Hz, 4H), 7.65 (t, J=7.6 Hz, 2H), 7.54 (t, J=8 Hz, 4H), 7.46 (d, J=7.2 Hz, 4H), 7.27 (t, J=7.2 Hz, 4H), 7.17 (t, J=7.2 Hz, 2H), 4.58 (s, 1H), 3.56 (s, 2H), 3.47 (s, 2H), 3.09 (br, 2H), 2.70 (s, 2H), 1.95 (s, 3H), 1.78 (s, 3H). $^{13}$C NMR (400 MHz, CDCl$_3$): δ (ppm) 202.1, 146.2, 143.2, 139.5, 136.7, 135.4, 135.2, 134.4, 131.1, 129.2, 128.9, 127.9, 127.3, 88.9, 73.6, 55.2, 54.0, 39.4, 36.6, 22.4, 16.2. IR (CH$_2$Cl$_2$, cm$^{-1}$): 3062, 2925, 2852, 1641, 1585, 1449, 1333, 1150, 1079, 1044. HRMS (ESI) calcd for C$_{37}$H$_{36}$NO$_5$S$_2$ [M$^+$Na]+ 638.2035. found 638.2033.

(1Z,6Z)-3-Benzhydryl-1,6-dimethyl-3,4-dihydrospiro[cyclopenta[d]azocine-8,2'-indene]-1',3',5(2H,7H,9H)-trione (3gd)

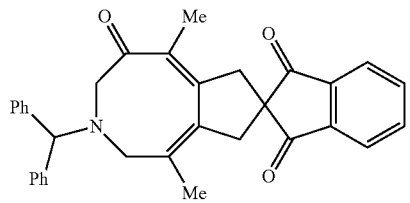 [SMILES: C/C1=C2\CC3(C\C2=C(/C)C(=O)CN(C(c2ccccc2)c2ccccc2)C1)C(=O)c1ccccc1C3=O]

The general procedure was used with diyne 1g (37.84 mg, 0.15 mmol), azetidinone 2d (29.9 mg, 0.13 mmol). The crude reaction mixture was purified by flash column chromatography on silica gel (30% EtOAc in hexanes) to afford the azocine 3gd as a pale yellow oil in 88% yield. $^1$H NMR (300 MHz, CDCl$_3$): δ (ppm) 7.99 (m, 2H), 7.86 (m, 2H), 7.53 (d, J=8 Hz, 4H), 7.28 (t, J=7.5 Hz, 4H), 7.16 (t, J=7.0 Hz, 2H), 4.74 (s, 1H), 3.52 (br, s, 2H), 3.02 (s, 2H), 2.92 (s, 2H), 2.90 (s 2H), 1.99 (s, 3H), 1.87 (s, 3H). $^{13}$C NMR (400 MHz, CDCl$_3$): δ (ppm) 202.8 202.6, 149.6, 143.5 141.4, 138.0, 137.3, 136.2, 134.0, 128.7, 127.9, 127.1, 123.8, 73.6, 55.5, 55.3, 54.2, 41.0 39.2 22.0, 15.8. IR (CH$_2$Cl$_2$, cm$^{-1}$): 3060, 3029, 2926, 2847, 1744, 1706, 1637, 1595, 1492, 1452, 1373, 1332, 1306, 1272, 1042, 920, 734, 705. HRMS (ESI) calcd for C$_{33}$H$_{29}$NO$_3$Na [M+Na]+ 510.2045. found 510.2048.

(1Z,6Z)-3-benzhydryl-1,6-dimethyl-5-oxo-8-phenyl-3,4,5,7,8,9-hexahydro-2H-cyclopenta[d]azocine-8-carbonitrile (3hd)

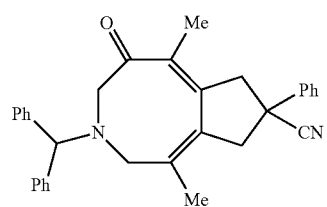 [SMILES: C/C1=C2\CC(C#N)(c3ccccc3)C\C2=C(/C)C(=O)CN(C(c2ccccc2)c2ccccc2)C1]

The general procedure was used with diyne 1 h (19.7 mg, 0.08 mmol), azetidinone 2d (17.6 mg, 0.07 mmol). The crude reaction mixture was purified by flash column chromatography on silica gel (15% EtOAc in hexanes) to afford the azocine 3hd as a pale yellow oil in 64% yield. $^1$H NMR (400 MHz, CDCl$_3$): δ (ppm) 7.54 (t, J=6.5 Hz, 4H), 7.46 (d, J=7.1 Hz, 2H), 7.40 (t, J=7.3 Hz, 2H), 7.36 (d, J=6.7 Hz, 1H), 7.30 (t, J=7.6 Hz, 4H), 7.18 (t, J=7.4 Hz, 2H), 4.75 (s, 1H), 3.62-3.49 (br, 2H), 3.46 (d, J=4.6 Hz, 1H), 3.42 (d, J=6.7 Hz, 1H), 3.13 (d, J=6.6 Hz, 1H), 3.09 (d, J=4.6 Hz, 1H), 3.02 (s, 2H), 2.06 (s, 3H), 1.92 (s, 3H) $^{13}$C NMR (400 MHz, CDCl$_3$): δ (ppm) 203.1, 147.3, 143.6, 143.5, 139.2, 136.9, 135.3, 129.0, 128.1, 127.5, 127.4, 126.0, 123.7, 73.9, 55.3, 54.5, 47.9, 45.4, 43.8, 22.3, 16.1. IR (CH$_2$Cl$_2$, cm$^{-1}$): 3060, 3027, 2933, 2869, 1661, 1491, 1451, 1375, 1315, 1276, 1205, 1177, 1074, 1026, 941, 742, 702, 639. HRMS (ESI) calcd for C$_{32}$H$_{31}$N$_2$O [M+H]+ 510.2045. found 510.2048.

(1Z,6Z)-3-Benzhydryl-1,6-dimethyl-3,4,8,9-tetrahydro-2H-cyclopenta[d]azocin-5(7H)-one (3id)

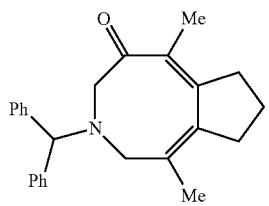 [SMILES: C/C1=C2\CCC\C2=C(/C)C(=O)CN(C(c2ccccc2)c2ccccc2)C1]

The general procedure for cycloaddition was used with diyne 1i (12.2 mg, 0.101 mmol, azetidinone 2d (20 mg, 0.0843). The crude reaction mixture was purified by flash column chromatography on silica gel (10% diethyl ether in pentane or 5% EtOAc in hexanes) to afford the eight-membered ring product 3id as a pale yellow oil in 68% yield. $^1$H NMR (400 MHz, CDCl$_3$): δ (ppm) 7.53 (d, J=7.2 Hz, 4H), 7.28 (t, J=7.2 Hz, 4H), 7.16 (t, J=7.2 Hz, 2H), 4.71 (s, 1H), 3.29-3.57 (br, 2H), 2.92 (s, 2H), 2.57 (t, J=7.6 Hz, 4H), 2.02 (s, 3H), 1.90 (s, 3H), 1.77 (p, J=7.6 Hz, 2H). $^{13}$C NMR (400 MHz, CDCl$_3$): δ (ppm) 203.1, 154.0, 143.8, 141.9, 135.5, 133.5, 128.7, 128.0, 127.1, 73.7, 53.4, 54.3, 35.1, 31.9, 22.1, 22.0, 15.8. IR (CH$_2$Cl$_2$, cm$^{-1}$): 2930, 1704, 1660, 1451, 1378, 1317, 1279. HRMS (ESI) calcd for C$_{25}$H$_{28}$NO [M+H]+ 358.2171. found 358.2172.

(1Z,6Z)-3-benzhydryl-1,6-dimethyl-3,4,7,9-tetrahydrospiro[cyclopenta[d]azocine-8,3'-oxetan]-5(2H)-one (3jd)

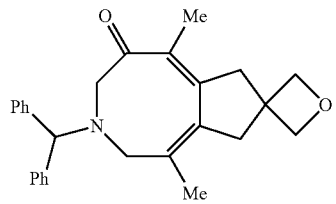 [SMILES: C/C1=C2\CC3(COC3)C\C2=C(/C)C(=O)CN(C(c2ccccc2)c2ccccc2)C1]

The general procedure for cycloaddition was used with diyne 1j (25.79 mg, 0.14 mmol, azetidinone 2d (34.3 mg, 0.16). The crude reaction mixture was purified by flash column chromatography on silica gel (30% EtOAc in hexanes) to afford the eight-membered ring product 3jd as a pale yellow oil in 87% yield. $^1$H NMR (400 MHz, CDCl$_3$): δ (ppm) 7.51 (d, J=7.6 Hz, 4H), 7.27 (t, J=8 Hz, 4H), 7.15 (t, J=7.6 Hz, 2H), 4.70 (s, 1H), 4.56 (m, 4H), 3.39 (br, s, 2H), 2.89 (m, 6H), 2.04 (s, 3H), 1.90 (s, 3H). $^{13}$C NMR (400 MHz, CDCl$_3$): δ (ppm) 202.8, 150.6, 143.5, 139.2, 136.8, 134.3, 128.7, 127.9, 127.1, 83.1, 73.6, 55.0, 54.3, 45.7 42.9, 42.6, 21.9, 15.7. IR (CH$_2$Cl$_2$, cm$^{-1}$): 3059, 3027, 2924, 2860, 1634, 1588, 1490, 1449, 1372, 1333, 1281, 1042, 978, 924, 834, 748, 705, 670. HRMS (ESI) calcd for C$_{27}$H$_{29}$NO$_2$Na [M+Na]+ 422.2096. found 422.2109.

(1'Z,6'Z)-1,3'-dibenzhydryl-1',6'-dimethyl-3',4',7',9'-tetrahydrospiro[azetidine-3,8'-cyclopenta[d]azocin]-5'(2'H)-one (3 kd)

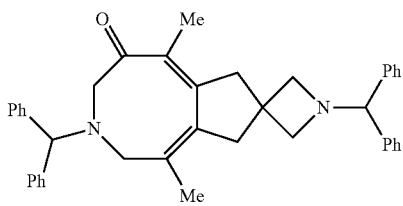 [SMILES: C/C1=C2\CC3(C\C2=C(/C)C(=O)CN(C(c2ccccc2)c2ccccc2)C1)CN(C(c1ccccc1)c1ccccc1)C3]

The general procedure for cycloaddition was used with diyne 1k (30.9 mg, 0.09 mmol, azetidinone 2d (18.7 mg, 0.08). The crude reaction mixture was purified by flash column chromatography on silica gel (10-30% EtOAc in hexanes) to afford the eight-membered ring product 3 kd as a pale yellow oil in 71% yield. $^1$H NMR (400 MHz, CDCl$_3$): δ (ppm) 7.51 (d, J=7.6 Hz, 4H), 7.41 (d, J=8 Hz, 4H), 7.26 (t, J=8 Hz, 7.2 Hz, 2H), 7.16 (m, 4H), 4.69 (s, 1H), 4.34 (s, 1H), 3.40 (br, s, 2H), 3.05 (m, 4H) 2.87 (s, 2H), 2.79 (s, 2H), 2.78 (s, 2H), 2.01 (s, 3H), 1.89 (s, 3H). $^{13}$C NMR (400 MHz, CDCl$_3$): δ (ppm) 202.9, 152.0, 143.6, 142.4, 140.2, 136.2, 133.9 128.7, 128.5, 127.9, 127.7, 127.2, 127.0, 78.3, 73.6, 65.3, 55.0, 54.3, 47.0 43.8, 37.3 22.0, 15.7. IR (CH$_2$Cl$_2$, cm$^{-1}$): 3060, 3027, 2925, 2818, 1635, 1590, 1492, 1452, 1337, 1305, 1278, 1248, 1072, 1030, 922, 744, 703. HRMS (ESI) calcd for C$_{40}$H$_{41}$N$_2$O [M+H]+ 565.3219. found 565.3218.

(1Z,6Z)-Dimethyl 1,6-dimethyl-5-oxo-4,5,7,9-tetrahydrocyclopenta[d]oxocine-8,8(2H)-dicarboxylate (3ae)

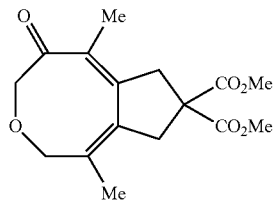 [SMILES: COC(=O)C1(C(=O)OC)CC2=C(\C)COCC(=O)/C(C)=C\2C1]

The general procedure was used with diyne 1a (78.68 mg, 0.33 mmol), oxetanone 2e (20.0 mg, 0.27 mmol). The crude product was purified by flash column chromatography on silica gel (50% Et$_2$O in hexanes) to afford the azocine 3ae as slightly pale yellow oil in 74% yield. $^1$H NMR (400 MHz, C$_6$D$_6$): δ (ppm) 3.99 (s, 2H), 3.98 (s, 2H), 3.73 (s, 6H), 3.19 (s, 2H), 3.17 (s, 2H), 1.99 (s, 3H), 1.90 (s, 3H). $^{13}$C NMR (400 MHz, C$_6$D$_6$): δ (ppm) 199.2, 171.4, 149.5, 140.0, 134.8, 134.5, 69.7, 68.5, 55.7, 53.2, 41.5, 38.8, 21.2, 15.7. IR (CH$_2$Cl$_2$, cm$^{-1}$): 2956, 2868, 2939, 2872, 1735, 1661, 1601, 1449, 1368, 1287, 1205, 1096, 1050, 1034, 920 864, 737, 704. HRMS (ESI) calcd for C$_{16}$H$_{20}$O$_6$Na [M+Na]+ 331.1158. found 331.1167.

(1Z,6Z)-Dimethyl 3-benzhydryl-6-methyl-5-oxo-4,5,7,9-tetrahydro-2H-cyclopenta[d]azocine-8,8(3H)-dicarboxylate (3ld)

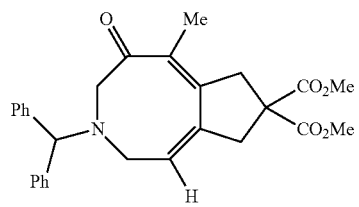 [SMILES: COC(=O)C1(C(=O)OC)CC2=C/CN(C(c3ccccc3)c3ccccc3)CC(=O)/C(C)=C\2C1]

The general procedure was used with diyne 1l (17.75 mg, 0.08 mmol), azetidinone 2d (15.8 mg, 0.06 mmol). The crude product was purified by flash column chromatography on silica gel (15% EtOAc in hexanes) to afford the azocine 3ld as pale yellow oil in 62% yield. $^1$H NMR (400 MHz, C$_6$D$_6$): δ (ppm) 7.53 (d, J=8.0 Hz, 4H), 7.30 (t, J=7.6 Hz, 4H), 7.19 (t, J=8.0 Hz, 2H) 6.08 (t, J=8.0 Hz, 1H), 4.70 (s, 1H), 3.77 (s, 6H), 3.41 (br, s, 2H) 3.24 (s, 2H), 3.23 (s, 2H), 2.94 (d, J=8.4 Hz, 2H), 1.93 (s, 3H). $^{13}$C NMR (400 MHz, C$_6$D$_6$): δ (ppm) 203.1, 171.4, 146.3, 144.1, 143.2, 135.5, 128.8, 128.0, 127.2, 126.6, 73.6, 56.1, 55.0, 53.3, 48.4, 43.0, 41.4, 15.8. IR (CH$_2$Cl$_2$, cm$^{-1}$): 3060, 3029, 2954, 2852, 1735, 1657, 1599, 1494, 1450, 1267, 1202, 1170, 1074, 734, 704. HRMS (ESI) calcd for C$_{28}$H$_{30}$NO$_5$ [M+H]+ 460.2124. found 460.2126.

The regiochemistry was assigned by 1d-NOESY experiment. The correlation of vinylic H with two methylene was observed.

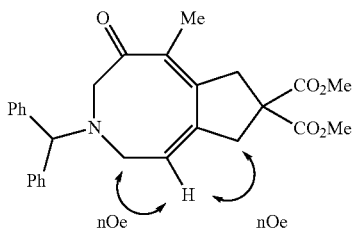 [SMILES: COC(=O)C1(C(=O)OC)CC2=C/CN(C(c3ccccc3)c3ccccc3)CC(=O)/C(C)=C\2C1]

(3aZ,9E)-6-Benzhydryl-4-ethoxy-9-methyl-3,5,6,7-tetrahydrofuro[3,4-d]azocin-8(1H)-one (3md)

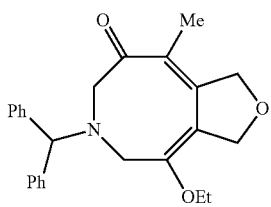

The general procedure was used with diyne 1m (13.1 mg, 0.08 mmol), azetidinone 2d (17.1 mg, 0.07 mmol). The crude product was purified by flash column chromatography on silica gel (10-15% EtOAc in hexanes) to afford the azocine 3md as pale yellow oil in 85% yield. $^1$H NMR (300 MHz, $C_6D_6$): δ (ppm) 7.53 (d, J=7.2 Hz, 4H), 7.26 (m, 4H), 7.20 (m, 2H), 4.76 (s, 1H), 4.72 (s, 2H), 4.61 (s, 2H), 3.85 (q, J=6.9 Hz, 2H), 3.55 (br, s, 2H), 3.06 (br, s, 2H), 1.80 (s, 3H), 1.24 (t, J=6.9 Hz, 3H). $^{13}$C NMR (400 MHz, $C_6D_6$): δ (ppm) 202.3, 154.3, 149.6, 142.8, 128.8, 128.0, 127.5, 121.8, 95.0, 74.0, 73.6, 71.1, 64.8 55.0, 49.2, 15.6, 15.0. IR ($CH_2Cl_2$, cm$^{-1}$): 3061, 3029, 2980 2931, 2853, 1723, 1654, 1632, 1587, 1492, 1452, 1376, 1347, 1277, 1208, 1145, 1109, 1031, 924, 761, 748, 705. HRMS (ESI) calcd for $C_{25}H_{27}NO_3Na$ [M+Na]+ 412.1889. found 412.1895.

The regiochemistry was assigned on the basis of 1d-NOESY experiment.

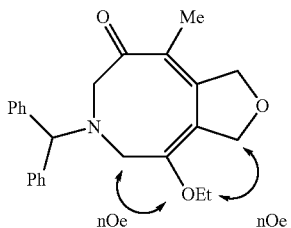 [SMILES: CCO/C1=C2\COC\C2=C(/C)C(=O)CN(C(c2ccccc2)c2ccccc2)C1]

1-Benzhydryl-1',4'-dimethyl-5',6',7',8'-tetrahydrospiro[azetidine-3,3'-isochromene] (3nd)

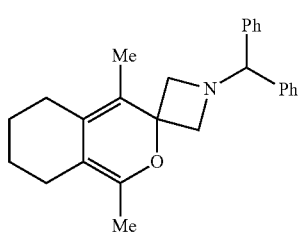 [SMILES: CC1=C2CCCCC2=C(C)C2(CN(C(c3ccccc3)c3ccccc3)C2)O1]

The general procedure was used with diyne 1n (14.93 mg, 0.11 mmol), azetidinone 2d (22.0 mg, 0.09 mmol). The crude product was purified by flash column chromatography on florisil (30% diethyl ether in pentane) to afford the azocine 3nd as colorless oil in 82% yield. $^1$H NMR (500 MHz, $C_6D_6$): δ (ppm) 7.44 (dd, J=8.1, 1.0 Hz, 4H), 7.12 (t, J=7.6 Hz, 4H), 7.01 (t, J=7.4 Hz, 2H), 4.33 (s, 1H), 3.59 (dd, J=6.9, 1.9 Hz, 2H), 3.31 (dd, J=6.9, 1.8 Hz, 2H), 2.15 (t, J=4.9 Hz, 2H), 2.06 (t, J=5.0 Hz, 2H), 2.03 (s, 3H), 1.76 (s, 3H), 1.46-1.38 (m, 4H). $^{13}$C NMR (500 MHz, $C_6D_6$): δ (ppm) 143.9, 143.5, 129.0, 128.9, 128.2, 127.6, 126.8, 120.0, 109.1, 79.0, 75.2, 66.5, 26.9, 25.8, 24.8, 24.5, 16.6, 13.1. IR ($CH_2Cl_2$, cm$^{-1}$): 3027, 2932, 2855, 1659, 1599, 1491, 1451, 1207, 1076, 1029, 743, 702. HRMS (ESI) calcd for $C_{26}H_{30}NO$ [M+H]+ 372.2327. found 372.2330.

g-HMBC summary: The following cross peaks were observed: H(4) and C(5); H(5) and C(6); H(6) and C(5); H(7) and C(6); H(10) and C(1); C(1); H(11); H(10) and C(11); H(10) and C(14); H(11) and C(1); H(11) and C(10); H(11) and C(14); H(12) and C(2); H(12) and C(3); H(13) and C(8).

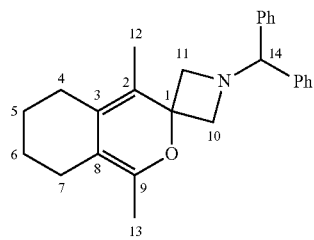 [SMILES: CC1=C2CCCCC2=C(C)C2(CN(C(c3ccccc3)c3ccccc3)C2)O1]

Tetraethyl 1-benzhydryl-1',4'-dimethylspiro[azetidine-3,3'-isochromene]-6',6',7',7'(5'H,8'H)-tetracarboxylate (3od)

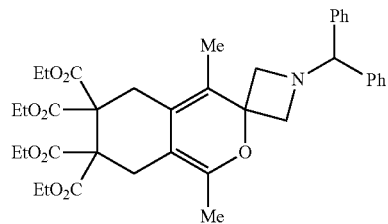 [SMILES: CCOC(=O)C1(C(=O)OCC)CC2=C(C)OC3(CN(C(c4ccccc4)c4ccccc4)C3)C(C)=C2CC1(C(=O)OCC)C(=O)OCC]

The general procedure was used with diyne 1o (41.2 mg, 0.09 mmol), azetidinone 2d (19.3 mg, 0.08 mmol). The crude product was purified by flash column chromatography on silica gel (10-30% EtOAc in hexanes) to afford the azocine 3od as colorless oil in 80% yield. $^1$H NMR (400 MHz, $C_6D_6$): δ (ppm) 7.41 (d, J=7.6 Hz, 4H), 7.24 (t, J=7.2 Hz, 4H), 7.15 (t, J=7.2 Hz, 2H), 4.37 (s 1H), 4.17 (m, 8H), 3.42 (d, J=8.4 Hz, 2H), 3.14 (d, J=8.4 Hz, 2H), 2.94 (s, 2H), 2.90 (s, 2H), 2.05 (s, 3H), 1.80 (s, 3H), 1.24 (m, 12H). $^{13}$C NMR (400 MHz, $C_6D_6$): δ (ppm) 170.1 169.9 144.6, 142.6, 128.5, 127.5 127.2, 122.8, 120.5, 105.5, 78.3, 74.9, 65.3, 61.88, 61.81, 58.5, 57.8, 31.3, 30.1 16.3, 14.0, 12.9. IR ($CH_2Cl_2$, cm$^{-1}$): 3061, 2984, 2939, 2872, 1735, 1661, 1601, 1449, 1368, 1287 1205, 1096, 1050, 1034 920 864, 737, 704. HRMS (ESI) calcd for $C_{38}H_{46}NO_9$ [M+H]+ 660.3173. found 660.3167.

Example 2

Crystallographic Characterization of Compound 3dd

A yellow prism shaped crystal 0.28×0.25×0.10 mm in size was mounted on a glass fiber with traces of viscous oil and then transferred to a Nonius KappaCCD diffractometer equipped with Mo Kα radiation (λ=0.71073 Å). Ten frames of data were collected at 150(1)K with an oscillation range of 1 deg/frame and an exposure time of 20 sec/frame (COLLECT Data Collection Software. Nonius B.V. 1998). Indexing and unit cell refinement based on all observed reflection from those ten frames, indicated a monoclinic P lattice. A total of 8408 reflections ($\Theta_{max}$=27.49°) were indexed, integrated and corrected for Lorentz, polarization and absorption effects using DENZO-SMN and SCALEPAC (Otwinowski et al. *Methods Enzymol.* 1997, 276, 307-326). Post refinement of the unit cell gave a=8.77710(10) Å, b=17.2725(5) Å, c=12.5333(3) Å, β=92.7903(16), and V=1897.83(7) Å$^3$. Axial photographs and systematic absences were consistent with the compound having crystallized in the monoclinic space group P2$_1$/a. The structure was solved by a combination of direct methods and heavy atom using SIR 97 ((Release 1.02)—A program for automatic solution and refinement of crystal structure. A. Altomare et al.).

All of the non-hydrogen atoms were refined with anisotropic displacement coefficients. Hydrogen atoms were located and refined isotropically using SHELXL97, University of Göttingen, Germany. (Includes SHELXS97, SHELXL97, CIFTAB—Sheldrick, G. M. (1997). Programs for Crystal Structure Analysis (Release 97-2)). The weighting scheme employed was w=1/[σ$^2$(F$_o$$^2$)+(0.0429P)$^2$+0.5798P] where P=(F$_o$$^2$+2F$_c$$^2$)/3. The refinement converged to R1=0.0452, wR2=0.096, and S=1.042 for 2914 reflections with I>2σ(I), and R1=0.0831, wR2=0.1126, and S=1.042 for 4340 unique reflections and 345 parameters (R1=Σ(||F$_o$|−|F$_c$||)/Σ|F$_o$|, wR2=[Σ(w(F$_o$$^2$−F$_c$$^2$)2)/Σ(F$_o$$^2$)$^2$]$^{1/2}$, and S=Goodness-of-fit on F$^2$=[Σ(w(F$_o$$^2$−F$_c$$^2$)$^2$/(n−p)]$^{1/2}$, where n is the number of reflections and p is the number of parameters refined). The maximum Δ/σ in the final cycle of the least-squares was 0, and the residual peaks on the final difference-Fourier map ranged from −0.197 to 0.333 e/Å$^3$. Scattering factors were taken from the International Tables for Crystallography, Volume C. (Maslen et al. International Tables for Crystallography: Mathematical, Physical and Chemical Tables, Vol. C, Chapter 6, Wilson, A. J. C., Ed.; Kluwer, Dordrecht, The Netherlands, 1992; pp. 476-516; Creagh et al. International Tables for Crystallography: mathematical, Physical and Chemical tables, Vol. C, Chapter 4 Wilson, A. J. C., Ed.; Kluwer, Dordrecht, The Netherlands, 1992; pp. 206-222; ORTEP3 for Windows—L. J. Farrugia, *J. Appl. Crystallogr.* 1997, 30, 565; WinGX A Windows Program for Crystal Structure Analysis. L. J. Farrugia, University of Glasgow, Glasgow, 1998).

An ORTEP diagram is illustrated in FIG. 1.

The invention claimed is:

1. A method of synthesizing a compound of formula (I):

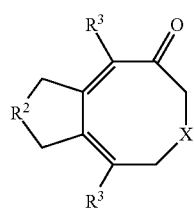

(I)

wherein:

X is selected from the group consisting of O and NR$^1$;
R$^1$ is selected from the group consisting of hydrogen, alkyl, and a nitrogen protecting group;

R$^2$ is selected from the group consisting of —C(O)O—, —C(O)—, —O—, —NR$^4$— and —CR$^5$$_2$—;

each R$^3$ is independently selected from the group consisting of hydrogen, alkyl, alkenyl, alkynyl, cycloalkyl, heterocyclyl, aryl, heteroaryl and cyano, any of which may be optionally substituted;

R$^4$ is selected from the group consisting of hydrogen, alkyl, and a nitrogen protecting group; and each R$^5$ is independently selected from the group consisting of hydrogen, alkyl, alkenyl, alkynyl, cycloalkyl, heterocyclyl, aryl, heteroaryl, acyl, alkoxy, amido, amino, carboxy, cyano, ester, halo, haloalkyl, hydroxy, nitro, phosphonate, sulfinyl, sulfonyl, sulfonate, sulfonamino and sulfonamido, any of which may be optionally substituted; or two R$^5$ are taken together with the atom to which they are attached to form an optionally substituted ring system;

the method comprising combining the following components to form a reaction mixture:

a) a compound of formula (II):

(II)

b) a compound of formula (III):

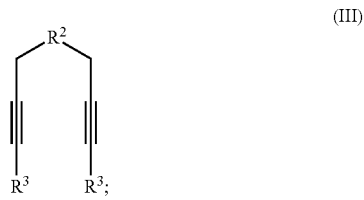

(III)

c) a nickel-containing compound; and
d) a ligand.

2. The method of claim 1, wherein the nickel-containing compound comprises nickel(0).

3. The method of claim 2, wherein the nickel-containing compound is bis(cyclooctadiene)nickel(0).

4. The method of claim 1, wherein the ligand is an N-heterocyclic carbene ligand.

5. The method of claim 1, wherein the ligand is 1,3-bis(2,6-diisopropylphenyl)imidazol-2-ylidene.

6. The method of claim 1, wherein the reaction mixture further comprises a solvent.

7. The method of claim 6, wherein the solvent is toluene.

8. The method of claim 1, wherein the nickel-containing compound is included in the reaction mixture in an amount of about 1 mol % to about 20 mol %.

9. The method of claim 1, wherein the ligand is included in the reaction mixture in an amount of about 5 mol % to about 30 mol %.

10. The method of claim 1, further comprising cooling the reaction mixture.

11. The method of claim 10, wherein the reaction mixture is cooled to a temperature of about −80° C. to about 20° C.

12. The method of claim 1, wherein the reaction mixture comprises an inert atmosphere.

13. The method of claim 1, further comprising purifying the compound of formula (I) from the reaction mixture.

14. The method of claim 1, wherein the concentration of the compound of formula (II) in the reaction mixture is about 0.01 M to about 1.0 M.

15. The method of claim 1, wherein X is $NR^1$, and $R^1$ is a nitrogen protecting group.

16. The method of claim 15, wherein $R^1$ is a tert-butyloxycarbonyl group or a benzhydryl group.

17. The method of claim 1, wherein the reaction mixture is reacted for about 2 hours to about 12 hours.

18. The method of claim 1, wherein the method provides the compound of formula (I) in about 20% yield to about 99% yield.

\* \* \* \* \*